US011453716B2

(12) United States Patent
Dubridge et al.

(10) Patent No.: US 11,453,716 B2
(45) **Date of Patent: *Sep. 27, 2022**

(54) SINGLE DOMAIN SERUM ALBUMIN BINDING PROTEIN

(71) Applicant: Harpoon Therapeutics, Inc., South San Francisco, CA (US)

(72) Inventors: Robert B. Dubridge, Belmont, CA (US); Bryan D. Lemon, Mountain View, CA (US); Richard J. Austin, San Francisco, CA (US); Luke Evnin, San Francisco, CA (US); Jeanmarie Guenot, San Francisco, CA (US)

(73) Assignee: HARPOON THERAPEUTICS, INC., South San Francisco, CA (US)

(*) Notice: Subject to any disclaimer, the term of this patent is extended or adjusted under 35 U.S.C. 154(b) by 867 days.

This patent is subject to a terminal disclaimer.

(21) Appl. No.: 16/161,986

(22) Filed: Oct. 16, 2018

(65) Prior Publication Data

US 2019/0031749 A1 Jan. 31, 2019

Related U.S. Application Data

(63) Continuation of application No. 15/600,582, filed on May 19, 2017, now Pat. No. 10,100,106.

(60) Provisional application No. 62/339,682, filed on May 20, 2016.

(51) Int. Cl.

| | |
|---|---|
| ***C07K 16/18*** | (2006.01) |
| ***C07K 16/28*** | (2006.01) |
| ***C07K 16/00*** | (2006.01) |
| *A61K 39/00* | (2006.01) |

(52) U.S. Cl.

CPC ............ *C07K 16/18* (2013.01); *C07K 16/005* (2013.01); *C07K 16/2809* (2013.01); *C07K 16/2887* (2013.01); *A61K 2039/505* (2013.01); *C07K 2317/31* (2013.01); *C07K 2317/33* (2013.01); *C07K 2317/565* (2013.01); *C07K 2317/567* (2013.01); *C07K 2317/569* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 4,816,567 | A | 3/1989 | Cabilly et al. |
| 4,943,533 | A | 7/1990 | Mendelsohn et al. |
| 5,061,620 | A | 10/1991 | Tsukamoto et al. |
| 5,199,942 | A | 4/1993 | Gillis |
| 5,225,539 | A | 7/1993 | Winter |
| 5,350,674 | A | 9/1994 | Boenisch et al. |
| 5,399,346 | A | 3/1995 | Anderson et al. |
| 5,530,101 | A | 6/1996 | Queen et al. |
| 5,565,332 | A | 10/1996 | Hoogenboom et al. |
| 5,580,859 | A | 12/1996 | Felgner et al. |
| 5,585,089 | A | 12/1996 | Queen et al. |
| 5,585,362 | A | 12/1996 | Wilson et al. |
| 5,589,466 | A | 12/1996 | Felgner et al. |
| 5,759,808 | A | 6/1998 | Casterman et al. |
| 5,766,886 | A | 6/1998 | Studnicka et al. |
| 5,773,292 | A | 6/1998 | Bander |
| 5,800,988 | A | 9/1998 | Casterman et al. |
| 5,840,526 | A | 11/1998 | Casterman et al. |
| 5,844,093 | A | 12/1998 | Kettleborough et al. |
| 5,858,358 | A | 1/1999 | June et al. |
| 5,859,205 | A | 1/1999 | Adair et al. |
| 5,874,541 | A | 2/1999 | Casterman et al. |
| 5,883,223 | A | 3/1999 | Gray |
| 6,005,079 | A | 12/1999 | Casterman et al. |
| 6,015,695 | A | 1/2000 | Casterman et al. |
| 6,107,090 | A | 8/2000 | Bander |
| 6,120,766 | A | 9/2000 | Hale et al. |
| 6,136,311 | A | 10/2000 | Bander |
| 6,326,193 | B1 | 12/2001 | Liu et al. |
| 6,331,415 | B1 | 12/2001 | Cabilly et al. |
| 6,352,694 | B1 | 3/2002 | June et al. |
| 6,407,213 | B1 | 6/2002 | Carter et al. |
| 6,534,055 | B1 | 3/2003 | June et al. |
| 6,548,640 | B1 | 4/2003 | Winter |
| 6,670,453 | B2 | 12/2003 | Frenken et al. |
| 6,692,964 | B1 | 2/2004 | June et al. |
| 6,759,518 | B1 | 7/2004 | Kontermann et al. |

(Continued)

FOREIGN PATENT DOCUMENTS

| | | | |
|---|---|---|---|
| CN | 1563092 | A | 1/2005 |
| CN | 101646689 | A | 2/2010 |

(Continued)

OTHER PUBLICATIONS

Almagro & Fransson, Frontiers in Bioscience 2008; 13:1619-33 (Year: 2008).*

De Genst et al., Dev Comp Immunol 2006; 30:187-98 (Year: 2006).*

Yoshinaga et al., J. Biochem 2008; 143:593-601 (Year: 2008).*

Baum et al. Antitumor activities of PSMA×CD3 diabodies by redirected T-cell lysis of prostate cancer cells. Immunotherapy 5(1):27-38 (2013).

(Continued)

*Primary Examiner* — Meera Natarajan

(74) *Attorney, Agent, or Firm* — Wilson Sonsini Goodrich & Rosati

(57) ABSTRACT

Disclosed herein are single domain serum albumins binding proteins with improved thermal stability, binding affinities, and robust aggregation profiles. Also described are multispecific binding proteins comprising a single domain serum albumin binding protein according to the instant disclosure. Pharmaceutical compositions comprising the binding proteins disclosed herein and methods of using such formulations are provided.

20 Claims, 5 Drawing Sheets

Specification includes a Sequence Listing.

(56) References Cited

U.S. PATENT DOCUMENTS 6,767,711 B2 7/2004 Bander
6,797,514 B2 9/2004 Berenson et al.
6,867,041 B2 3/2005 Berenson et al.
6,887,466 B2 5/2005 June et al.
6,905,680 B2 6/2005 June et al.
6,905,681 B1 6/2005 June et al.
6,905,874 B2 6/2005 Berenson et al.
7,060,808 B1 6/2006 Goldstein et al.
7,067,318 B2 6/2006 June et al.
7,144,575 B2 12/2006 June et al.
7,163,680 B2 1/2007 Bander
7,172,869 B2 2/2007 June et al.
7,175,843 B2 2/2007 June et al.
7,232,566 B2 6/2007 June et al.
7,247,301 B2 7/2007 Van De Winkel et al.
7,262,276 B2 8/2007 Huang et al.
7,595,378 B2 9/2009 Van De Winkel et al.
7,666,414 B2 2/2010 Bander
7,723,484 B2 5/2010 Beidler et al.
7,807,162 B2 10/2010 Silence
7,850,971 B2 12/2010 Maddon et al.
7,939,072 B2 5/2011 Yarden et al.
8,114,965 B2 2/2012 Maddon et al.
8,188,223 B2 5/2012 Beirnaert et al.
8,236,308 B2 8/2012 Kischel et al.
8,470,330 B2 6/2013 Schuelke et al.
8,623,356 B2 1/2014 Christopherson et al.
8,629,244 B2 1/2014 Kolkman et al.
8,703,135 B2 4/2014 Beste et al.
8,784,821 B1 7/2014 Kufer et al.
8,846,042 B2 9/2014 Zhou
8,907,071 B2 12/2014 Sullivan et al.
8,937,164 B2 1/2015 Descamps et al.
9,169,316 B2 10/2015 Baty et al.
9,309,327 B2 4/2016 Humphreys et al.
9,327,022 B2 5/2016 Zhang et al.
9,340,621 B2 5/2016 Kufer et al.
9,708,412 B2 7/2017 Baeuerle et al.
9,920,115 B2 3/2018 Dubridge et al.
10,066,016 B2 9/2018 Dubridge et al.
10,100,106 B2 10/2018 Dubridge et al.
10,428,120 B2 10/2019 Kontermann et al.
11,180,563 B2 11/2021 Wesche et al.
2002/0015704 A1 2/2002 Bander
2002/0051780 A1 5/2002 Lindhofer et al.
2003/0031673 A1 2/2003 Bander
2003/0092892 A1 5/2003 Frenken et al.
2004/0101519 A1 5/2004 June et al.
2005/0042664 A1 2/2005 Wu et al.
2005/0048617 A1 3/2005 Wu et al.
2005/0100543 A1 5/2005 Hansen et al.
2005/0175606 A1 8/2005 Huang et al.
2006/0034810 A1 2/2006 Riley et al.
2006/0046971 A1 3/2006 Stuhler et al.
2006/0121005 A1 6/2006 Berenson et al.
2006/0228364 A1 10/2006 Dennis et al.
2006/0252096 A1 11/2006 Zha et al.
2007/0014794 A1 1/2007 Carter et al.
2007/0178082 A1 8/2007 Silence et al.
2007/0269422 A1 11/2007 Beirnaert et al.
2008/0069772 A1 3/2008 Stuhler et al.
2008/0260757 A1 10/2008 Holt et al.
2009/0259026 A1 10/2009 Tomlinson et al.
2010/0022452 A1 1/2010 Silence
2010/0122358 A1 5/2010 Brueggemann et al.
2010/0150918 A1 6/2010 Kufer et al.
2010/0166734 A1 7/2010 Dolk
2010/0189651 A1 7/2010 Stagliano et al.
2010/0189727 A1 7/2010 Rodeck et al.
2010/0266531 A1 10/2010 Hsieh et al.
2010/0291112 A1 11/2010 Kellner et al.
2010/0311119 A1 12/2010 Hermans et al.
2011/0129458 A1 6/2011 Dolk et al.
2011/0165621 A1 7/2011 Dreier et al.
2011/0262439 A1 10/2011 Kufer et al.
2011/0275787 A1 11/2011 Kufer et al.
2011/0313135 A1 12/2011 Vanhove et al.
2012/0039899 A1 2/2012 Olsen et al.
2012/0231024 A1 9/2012 Elsaesser-Beile et al.
2012/0237977 A1 9/2012 Daugherty et al.
2012/0328619 A1 12/2012 Fey et al.
2013/0017200 A1 1/2013 Scheer et al.
2013/0136744 A1 5/2013 Bouche et al.
2013/0197201 A1 8/2013 Vasquez et al.
2013/0266568 A1 10/2013 Brinkmann et al.
2013/0267686 A1 10/2013 Brinkmann et al.
2013/0273055 A1 10/2013 Borges et al.
2013/0330335 A1 12/2013 Bremel et al.
2014/0004121 A1 1/2014 Fanslow, III et al.
2014/0023664 A1 1/2014 Lowman et al.
2014/0045195 A1 2/2014 Daugherty et al.
2014/0073767 A1 3/2014 Lee et al.
2014/0088295 A1 3/2014 Smith et al.
2014/0205601 A1 7/2014 Beirnaert et al.
2014/0242075 A1 8/2014 Parren et al.
2014/0302037 A1 10/2014 Borges et al.
2014/0322218 A1 10/2014 Xiao et al.
2015/0037334 A1 2/2015 Kufer et al.
2015/0056206 A1 2/2015 Zhou
2015/0064169 A1 3/2015 Wang et al.
2015/0079088 A1 3/2015 Lowman et al.
2015/0079093 A1 3/2015 Stuhler
2015/0093336 A1 4/2015 Van Ginderachter et al.
2015/0174268 A1 6/2015 Li et al.
2015/0183875 A1 7/2015 Cobbold et al.
2015/0232557 A1 8/2015 Tan et al.
2015/0274836 A1 10/2015 Ho et al.
2015/0274844 A1 10/2015 Blankenship et al.
2016/0017058 A1 1/2016 Kim et al.
2016/0024174 A1 1/2016 Odunsi et al.
2016/0032011 A1 2/2016 Zhang et al.
2016/0032019 A1 2/2016 Xiao et al.
2016/0039942 A1 2/2016 Cobbold et al.
2016/0068605 A1 3/2016 Nemeth et al.
2016/0115241 A1 4/2016 Yan et al.
2016/0130331 A1 5/2016 Stull et al.
2016/0215063 A1 7/2016 Bernett et al.
2016/0229913 A1 8/2016 Bosques et al.
2016/0251440 A1 9/2016 Roobrouck et al.
2016/0257721 A1 9/2016 Lieber et al.
2016/0319040 A1 11/2016 Dreier et al.
2016/0340444 A1 11/2016 Baeuerle et al.
2016/0355842 A1 12/2016 Parks et al.
2017/0029502 A1 2/2017 Raum et al.
2017/0037149 A1 2/2017 Raum et al.
2017/0152316 A1 6/2017 Cobbold et al.
2017/0158771 A1 6/2017 Glennie et al.
2017/0204164 A1 7/2017 Himmler et al.
2017/0275373 A1 9/2017 Kufer et al.
2017/0298149 A1 10/2017 Baeuerle et al.
2017/0334997 A1 11/2017 Dubridge et al.
2017/0362310 A1 12/2017 Shoemaker
2017/0369563 A1 12/2017 Dubridge et al.
2018/0016323 A1 1/2018 Brandenburg et al.
2018/0134789 A1 5/2018 Baeuerle et al.
2018/0148508 A1 5/2018 Wang et al.
2018/0161428 A1 6/2018 Dubridge et al.
2018/0162949 A1 6/2018 Baeuerle et al.
2018/0326060 A1 11/2018 Wesche et al.
2018/0327508 A1 11/2018 Wesche et al.
2018/0346601 A1 12/2018 Dettling et al.
2019/0092862 A1 3/2019 Cui et al.
2019/0225702 A1 7/2019 Baeuerle et al.
2020/0095340 A1 3/2020 Wesche et al.
2020/0115461 A1 4/2020 Evnin et al.
2020/0148771 A1 5/2020 Paeuerle et al.
2021/0171649 A1 6/2021 Wesche et al.
2021/0179735 A1 6/2021 Baeuerle et al.
2021/0269530 A1 9/2021 Lin et al.
2021/0284728 A1 9/2021 Lin et al.
2021/0292421 A1 9/2021 Lin et al.
2021/0355219 A1 11/2021 Lin et al.
2022/0017626 A1 1/2022 Wesche et al.

(56) References Cited

U.S. PATENT DOCUMENTS

| | | | |
|---|---|---|---|
| 2022/0054544 | A1 | 2/2022 | Lin et al. |
| 2022/0098311 | A1 | 3/2022 | Wesche et al. |
| 2022/0112297 | A1 | 4/2022 | Wesche et al. |

FOREIGN PATENT DOCUMENTS

| | | | |
|---|---|---|---|
| CN | 105968201 | A | 9/2016 |
| CN | 105968204 | A | 9/2016 |
| CN | 109593786 | A | 4/2019 |
| EP | 0239400 | A2 | 9/1987 |
| EP | 0519596 | A1 | 12/1992 |
| EP | 0592106 | A1 | 4/1994 |
| EP | 1378520 | A1 | 1/2004 |
| EP | 1736484 | A1 | 12/2006 |
| EP | 2336179 | A1 | 6/2011 |
| FR | 901228 | A | 7/1945 |
| JP | 2005501517 | A | 1/2005 |
| JP | 2005518789 | A | 6/2005 |
| JP | 2016500655 | A | 1/2016 |
| JP | 2019052750 | A | 4/2019 |
| WO | WO-9109967 | A1 | 7/1991 |
| WO | WO-9307105 | A1 | 4/1993 |
| WO | WO-9404678 | A1 | 3/1994 |
| WO | WO-9937681 | A2 | 7/1999 |
| WO | WO-0043507 | A1 | 7/2000 |
| WO | WO-0190190 | A2 | 11/2001 |
| WO | WO-0196584 | A2 | 12/2001 |
| WO | WO-02085945 | A2 | 10/2002 |
| WO | WO-03025020 | A1 | 3/2003 |
| WO | WO-03035694 | A2 | 5/2003 |
| WO | WO-03064606 | A2 | 8/2003 |
| WO | WO 2004/003019 | * | 1/2004 |
| WO | WO-2004003019 | A2 | 1/2004 |
| WO | WO-2004041867 | A2 | 5/2004 |
| WO | WO-2004042404 | A1 | 5/2004 |
| WO | WO-2004049794 | A2 | 6/2004 |
| WO | WO-2004099249 | A2 | 11/2004 |
| WO | WO-2006020258 | A2 | 2/2006 |
| WO | WO-2006122787 | A1 | 11/2006 |
| WO | WO-2007024715 | A2 | 3/2007 |
| WO | WO-2007042261 | A2 | 4/2007 |
| WO | WO-2007062466 | A1 | 6/2007 |
| WO | WO-2007115230 | A2 | 10/2007 |
| WO | WO-2008028977 | A2 | 3/2008 |
| WO | WO-2009025846 | A2 | 2/2009 |
| WO | WO-2009030285 | A1 | 3/2009 |
| WO | WO-2009147248 | A2 | 12/2009 |
| WO | WO-2010003118 | A1 | 1/2010 |
| WO | WO-2010037836 | A2 | 4/2010 |
| WO | WO-2010037837 | A2 | 4/2010 |
| WO | WO-2010081173 | A2 | 7/2010 |
| WO | WO-2011039368 | A2 | 4/2011 |
| WO | WO-2011051327 | A2 | 5/2011 |
| WO | WO-2011117423 | A1 | 9/2011 |
| WO | WO-2012131053 | A1 | 10/2012 |
| WO | WO-2012138475 | A1 | 10/2012 |
| WO | WO-2012158818 | A2 | 11/2012 |
| WO | WO-2012163805 | A1 | 12/2012 |
| WO | WO-2012175400 | A1 | 12/2012 |
| WO | WO-2013036130 | A1 | 3/2013 |
| WO | WO-2013072406 | A1 | 5/2013 |
| WO | WO-2013072415 | A1 | 5/2013 |
| WO | WO-2013104804 | A2 | 7/2013 |
| WO | WO-2013110531 | A1 | 8/2013 |
| WO | WO-2013126712 | A1 | 8/2013 |
| WO | WO-2013128027 | A1 | 9/2013 |
| WO | WO-2013128194 | A1 | 9/2013 |
| WO | WO-2014033304 | A2 | 3/2014 |
| WO | WO-2014047231 | A1 | 3/2014 |
| WO | WO-2014052064 | A1 | 4/2014 |
| WO | WO-2014138306 | A1 | 9/2014 |
| WO | WO-2014140358 | A1 | 9/2014 |
| WO | WO-2014144689 | A1 | 9/2014 |
| WO | WO-2014151910 | A1 | 9/2014 |
| WO | WO-2015103072 | A1 | 7/2015 |
| WO | WO-2015146437 | A1 | 10/2015 |
| WO | WO-2015150447 | A1 | 10/2015 |
| WO | WO-2015184207 | A1 | 12/2015 |
| WO | WO-2016009029 | A1 | 1/2016 |
| WO | WO-2016034044 | A1 | 3/2016 |
| WO | WO-2016046778 | A2 | 3/2016 |
| WO | WO-2016055551 | A1 | 4/2016 |
| WO | WO-2016087531 | A1 | 6/2016 |
| WO | WO-2016105450 | A2 | 6/2016 |
| WO | WO-2016130819 | A2 | 8/2016 |
| WO | WO-2016171999 | A2 | 10/2016 |
| WO | WO-2016179003 | A1 | 11/2016 |
| WO | WO-2016182064 | A1 | 11/2016 |
| WO | WO-2016187101 | A2 | 11/2016 |
| WO | WO-2016187594 | A1 | 11/2016 |
| WO | WO-2016210447 | A1 | 12/2016 |
| WO | WO-2017021356 | A1 | 2/2017 |
| WO | WO-2017025038 | A1 | 2/2017 |
| WO | WO-2017025698 | A1 | 2/2017 |
| WO | WO-2017027392 | A1 | 2/2017 |
| WO | WO-2017031104 | A1 | 2/2017 |
| WO | WO-2017041749 | A1 | 3/2017 |
| WO | WO-2017079528 | A1 | 5/2017 |
| WO | WO-2017134134 | A1 | 8/2017 |
| WO | WO-2017136549 | A1 | 8/2017 |
| WO | WO-2017156178 | A1 | 9/2017 |
| WO | WO-2017161206 | A1 | 9/2017 |
| WO | WO-2018017863 | A1 | 1/2018 |
| WO | WO-2018026953 | A1 | 2/2018 |
| WO | WO-2018067993 | A1 | 4/2018 |
| WO | WO-2018071777 | A1 | 4/2018 |
| WO | WO-2018083204 | A1 | 5/2018 |
| WO | WO-2018098354 | A1 | 5/2018 |
| WO | WO-2018098356 | A1 | 5/2018 |
| WO | WO-2018133877 | A1 | 7/2018 |
| WO | WO-2018136725 | A1 | 7/2018 |
| WO | WO-2018160671 | A1 | 9/2018 |
| WO | WO-2018160754 | A2 | 9/2018 |
| WO | WO-2018165619 | A1 | 9/2018 |
| WO | WO-2018204717 | A1 | 11/2018 |
| WO | WO-2018209298 | A1 | 11/2018 |
| WO | WO-2018209304 | A1 | 11/2018 |
| WO | WO-2018232020 | A1 | 12/2018 |
| WO | WO-2019025983 | A1 | 2/2019 |
| WO | WO-2019075359 | A1 | 4/2019 |
| WO | WO-2019075378 | A1 | 4/2019 |
| WO | WO-2019222278 | A1 | 11/2019 |
| WO | WO-2019222282 | A1 | 11/2019 |
| WO | WO-2019222283 | A1 | 11/2019 |
| WO | WO-2019229701 | A2 | 12/2019 |
| WO | WO-2020060593 | A1 | 3/2020 |
| WO | WO-2020061482 | A1 | 3/2020 |
| WO | WO-2020061526 | A1 | 3/2020 |
| WO | WO-2020069028 | A1 | 4/2020 |
| WO | WO-2020232303 | A1 | 11/2020 |
| WO | WO-2021097060 | A1 | 5/2021 |
| WO | WO-2021168303 | A1 | 8/2021 |
| WO | WO-2021231434 | A1 | 11/2021 |

OTHER PUBLICATIONS

Harmsen et al. Properties, production, and applications of camelid single-domain antibody fragments. Appl. Microbiol. Biotechnol. 77:13-22 (2007).

PCT/US2019/052270 International Search Report and Written Opinion dated Mar. 5, 2020.

U.S. Appl. No. 15/821,498 Office Action dated Apr. 21, 2020.

U.S. Appl. No. 15/821,530 Office Action dated Apr. 22, 2020.

U.S. Appl. No. 16/583,070 Office Action dated Mar. 3, 2020.

Zabetakis et al. Contributions of the complementarity determining regions to the thermal stability of a single-domain antibody. PLoS One 8(10):e77678 (2013).

Almagro et al. Humanization of antibodies. Front Biosci 13:1619-1633 (2008).

Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).

(56) References Cited

OTHER PUBLICATIONS

Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 14, 2018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Bedouelle et al. Diversity and junction residues as hotspots of binding energy in an antibody neutralizing the dengue virus. FEBS J 273(1):34-46 (2006).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Casset et al. A peptide mimetic of an anti-CD4 monoclonal antibody by rational design. Biochemical and Biophysical Research Communication 307:198-205 (2003).
Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Chothia et al. Canonical structures for the hypervariable regions of immunoglobulins. J Mol Biol 196(4):901-917 (1987).
Co-pending U.S. Appl. No. 16/159,545, filed Oct. 12, 2018.
Co-pending U.S. Appl. No. 16/159,554, filed Oct. 12, 2018.
Corso et al. Real-time detection of mesothelin in pancreatic cancer cell line supernatant using an acoustic wave immunosensor. Cancer Detect Prey 30:180-187 (2006).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Document D28—Investigation of human CD3ϵ variants binding to monoclonal antibodies. Submitted by Pfizer to the European Patent Register on Apr. 30, 2014 in connection with their opposition to the EP2155783 patent. (3 pages) (2014).
Document D78—CD3ϵ N-terminal peptide bound to the CDRs of SP24. Submitted by Janssen Biotech to the European Patent Register on Mar. 18, 2016 in connection with their opposition to the EP2155783 patent (1 page) (2016).
Document D79—Interactions between CD3ϵ and SP34 CDR residues. CD3ϵ residues are in ellipses, SP34 CDR residues are in boxes. Submitted by Janssen Biotech to the European Patent Register on Mar. 18, 2016 in connection with their opposition to the EP2155783 patent (1 page) (2016) .
Document D83—Alignment of variable domains from the prior art and the patent. Submitted by Janssen Biotech to the European Patent Register on Mar. 18, 2016 in connection with their opposition to the EP2155783 patent (1 page) (2016).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Giusti et al. Somatic diversification of S107 from an antiphosphocholine to an anti-DNA autoantibody is due to a single base change in its heavy chain variable region. PNAS USA 84(9):2926-30 (1987).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Harding et al. The immunogenicity of humanized and fully human antibodies: residual immunogenicity resides in the CDR regions. MAbs 2(3):256-265 (2010).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).
Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prey 15:1014-1020 (2006).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short lived drugs. Protien Eng Des Sel 21(5):283-288 (2008).
Hutchinson et al. Mutagenesis at a specific position in a DNA sequence. J Biol Chem 253:6551-6560 (1978).
Janssen letter—Submission under Rule 116 EPC. Submitted by Janssen Biotech to the European Patent Register on Mar. 18, 2016 in connection with their opposition to the EP2155783 patent (6 pages) (2016).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kojima et al. Molecular cloning and expression of megakaryocyte potentiating factor cDNA. J Biol Chem 270:21984-21990 (1995).

(56) References Cited

OTHER PUBLICATIONS

Le Gall et al. Immunosuppressive properties of anti-CD3 single-chain Fv and diabody. J Immunol Methods 285(1): 111-127 (2004).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
Maccallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Mirsky et al. Antibody-Specific Model of Amino Acid Substitution for Immunological Inferences from Alignments of Antibody Sequences. Mol. Biol. Evol. 32(3):806-819 (2014).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Mueller et al. Improved pharmacokinetics of recombinant bispecific antibody molecules by fusion to human serum albumin. J Bio Chem 282(17):12650-12660 (2007).
Muller et al. Improving the pharmacokinetic properties of biologics by fusion to an anti-HSA shark VNAR domain. MAbs 4(6):673-685 (2012).
Muul et al. Persistence and expression of the adenosine deaminase gene for 12 years and immune reaction to gene transfer components: long-term results of the first clinical gene therapy trial. Blood 101(7):2563-2569 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Nelson et al. Antibody fragments Hope and Hype. mAbs 2(1):77-83 (2010).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by RTX. J Immunol 183:749-758 (2009).
PCT/US2016/033644 International Preliminary Report on Patentability dated Nov. 30, 2017.
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017056530 International Search Report and Written Opinion dated Jan. 23, 2018.
PCT/US2017/063121 International Search Report and Written Opinion dated Mar. 26, 2018.
PCT/US2017/063121 Invitation to Pay Additional Fees dated Feb. 1, 2018.
PCT/US2017/063126 International Search Report and Written Opinion dated Apr. 5, 2018.
PCT/US2017/063126 Invitation to Pay Additional Fees dated Feb. 1, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/030983 Invitation to Pay Additional Fees dated Jul. 31, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 Invitation to Pay Additional Fees dated Dec. 19, 2018.
PCT/US2018/055682 Invitation to Pay Additional Fees dated Jan. 8, 2019.
PCT/US2018/32418 Invitation to Pay Additional Fees dated Jul. 23, 2018.
PCT/US2018/32427 Invitation to Pay Additional Fees dated Jul. 24, 2018.
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Presta et al. Humanization of an antibody directed against IgE. J Immunol 151:2623-2632 (1993).
Riechmann et al. Single domain antibodies: comparison of camel VH and camelised human VH domains. J Immunol Methods 231(1-2):25-38 (1999).
Rosok et al. A Combinatorial Library Strategy for the Rapid Humanization of Anticarcinoma BR96 Fab. J Biol Chem 271:22611-22618 (1996).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Saerens et al. Identification of a universal VHH framework to graft non-canonical antigen-binding loops of camel single-domain antibodies. J. Mol. Biol. 352(3):597-607 (2005).
Schmittgen et al. Expression of prostate specific membrane antigen and three alternatively spliced variants of PSMA in prostate cancer patients. Int J Cancer 107:323-329 (2003).
Sims et al. A humanized CD18 antibody can block function without cell destruction. J Immunol., 151 (1993): 2296-2308.
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Su et al. PSMA specific single chain antibody-mediated targeted knockdown of Notch1 inhibits human prostate cancer cell proliferation and tumor growth. Cancer Lett. 338 (2): 282-291 (2013).

(56) References Cited

OTHER PUBLICATIONS

Tang et al. A human single-domain antibody elicits potent antitumor activity by targeting an epitope in mesothelin close to the cancer cell surface. Mol. Cancer Thera 12(4):416-426 (2013).
Thomas et al. Mesothelin-specific CD8(+) T cell responses provide evidence of in vivo cross-priming by antigen-presenting cells in vaccinated pancreatic cancer patients. J Exp Med 200:297-306 (2004).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/704,620 Office Action dated Oct. 26, 2017.
U.S. Appl. No. 15/821,498 Office Action dated Oct. 26, 2018.
U.S. Appl. No. 15/821,530 Office Action dated Sep. 25, 2018.
U.S. Appl. No. 15/977,988 Preinterview First Office Action dated Jan. 25, 2019.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Vaughan et al. Human antibodies by design. Nature Biotech 16:535-539 (1998).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yu et al. Rationalization and design of the complementarity determining region sequences in an antibody-antigen recognition interface. PLoS One 7(3):e33340 (2012).
Zare et al. Production of nanobodies against prostate-specific membrane antigen (PSMA) recognizing LnCaP cells. Int. J. Biol. Markers 29(2):e169-e179 (2014).
Zhu et al. COMBODY: one-domain antibody multimer with improved avidity. Immunology and Cell Biology 88(6):667-675 (2010).
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1977).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Caldas et al. Design and synthesis of germline-based hemi-humanized single-chain Fv against the CD18 surface antigen. Protein Eng 13(5):353-360 (2000).
Carter et al. PD-1: PD-L inhibitory pathway affects both CD4(+) and CD8(+) T cells and is overcome by IL-2. Eur J Immunol 32:634-643 (2002).
Choi et al. Engineering of Immunoglobulin Fc heterodimers using yeast surface-displayed combinatorial Fc library screening. PLOS One 10(12):e0145349 (2015).
Chothia, et al. Conformations of immunoglobulin hypervariable regions. Nature 342(6252):877-83 (1989).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Dao et al. Targeting the intracellular WT1 oncogene product with a therapeutic human antibody. Sci Transi Med 5(176):176ra33 (2013).
De Genst et al. Antibody repertoire development in camelids. Dev Comp Immunol 30(1-2):187-198 (2006).
Dong et al. B7-H1 pathway and its role in the evasion of tumor immunity. J Mol Med 81:281-287 (2003).
Elango et al. Optimized transfection of mRNA transcribed from a d(A/T)100 tail-containing vector. Biochim Biophys Res Commun 330:958-966 (2005).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Grupp et al. Chimeric antigen receptor-modified T cells for acute lymphoid leukemia. NEJM 368:1509-1518 (2013).
Haanen et al. Selective expansion of cross-reactive CD8(+) memory T cells by viral variants. J Exp Med 190(9):1319-1328 (1999).
Ho et al. Mesothelin is shed from tumor cells. Cancer Epidemiol Biomarkers Prey 15:1751 (2006).
Hollinger et al. "Diabodies": Small bivalent and bispecific antibody fragments . PNAS USA 90:6444 6448 (1993).
Huston et al. Protein engineering of antibody binding sites: recovery of specific activity in an anti-digoxin single-chain Fv analogue produced in *Escherichia coli*. PNAS USA 85(16):5879-5883 (1988).
Izumoto et al. Phase II clinical trial of Wilms tumor 1 peptide vaccination for patients with recurrent glioblastoma multiforme. J Neurosurg 108:963-971 (2008).
Jones et al. Replacing the complementarity-determining regions in a human antibody with those from a mouse. Nature 321:522-525 (1986).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Konishi et al. B7-H1 expression on non-small cell lung cancer cells and its relationship with tumor-infiltrating lymphocytes and their PD-1 expression. Clin Cancer Res 10:5094-5100 (2004).
Latchman et al. PD-L2 is a second ligand for PD-1 and inhibits T cell activation. Nat Immunol 2:261-268 (2001).
Lowman et al. Monovalent phage display: A method for selecting variant proteins from random libraries. Methods 3:205-216 (1991).

(56) References Cited

OTHER PUBLICATIONS

Milone et al. Chimeric receptors containing CD137 signal transduction domains mediate enhanced survival of T cells and increased antileukemic efficacy in vivo. Mol Ther 17(8):1453-1464 (2009).
Mumtaz et al. Design of liposomes for circumventing the reticuloendothelial cells. Glycobiology 5:505-10 (1991).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Padlan. A possible procedure for reducing the immunogenicity of antibody variable domains while preserving their ligand-binding properties. Mol Immunol 28(4-5):489-498 (1991).
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052206 Invitation to Pay Additional Fees dated Dec. 23, 2019.
PCT/US2019/052270 Invitation to Pay Additional Fees dated Jan. 9, 2020.
PCT/US2019/053017 International Search Report and Written Opinion dated Jan. 31, 2020.
PCT/US2019/053017 Invitation to Pay Additional Fees dated Nov. 27, 2019.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta. Antibody Engineering. Curr Op Struct Biol 2:593-596 (1992).
Riechmann et al. Reshaping human antibodies for therapy. Nature, 332.6162:323-7 (1988).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Sadelain et al. The basic principles of chimeric antigen receptor design. Cancer Discov. 3(4):388-98 (2013).
Sandhu. A rapid procedure for the humanization of monoclonal antibodies. Gene 150(2):409-410 (1994).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
Scheraga. Predicting three-dimensional structures of oligopeptides. Rev Computational Chem 3:73-142 (1992).
Sergeeva et al. An anti-PR1/HLA-A2 T-cell receptor-like antibody mediates complement-dependent cytotoxicity against acute myeloid leukemia progenitor cells. Blood 117(16):4262-4272 (2011).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Tan et al. "Superhumanized" antibodies: reduction of immunogenic potential by complementarity-determining region grafting with human germline sequences: application to an anti-CD28. J Immunol 169:1119-1125 (2002).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/630,259 Office Action dated Dec. 30, 2019.
U.S. Appl. No. 15/977,988 Office Action dated Aug. 20, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Oct. 1, 2019.
Van Der Linden et al. Induction of immune responses and molecular cloning of the heavy chain antibody repertoire of Lama glama. J Immunol Methods 240:185-195 (2000).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Willemsen et al. A phage display selected fab fragment with MHO class I-restricted specificity for MAGE-A1 allows for retargeting of primary human T lymphocytes. Gene Ther 8(21):1601-1608 (2001).
Yan et al. Engineering upper hinge improves stability and effector function of a human IgG1. J. Biol. Chem. 287:5891 (2012).
Yoshinaga et al. Ig L-chain shuffling for affinity maturation of phage library-derived human anti-human MCP-1 antibody blocking its chemotactic activity. J Biochem 143(5):593-601 (2008).
Co-pending U.S. Appl. No. 16/773,806, filed Jan. 27, 2020.
Co-pending U.S. Appl. No. 16/773,843, filed Jan. 27, 2020.
Co-pending U.S. Appl. No. 16/802,007, filed Feb. 26, 2020.
Zhang et al. New High Affinity Monoclonal Antibodies Recognize Non-Overlapping Epitopes on Mesothelin for Monitoring and Treating Mesothelioma. Sci Rep 5:9928 (2015).
Chen, Xiaoying et al. Fusion protein linkers: Property, design and functionality. Advanced Drug Delivery Reviews 65:1357-1369 (2013).
Dennis et al. Imaging Tumors with an Albumin-Binding Fab, a Novel Tumor-Targeting Agent. Cancer Res 67(1):254-61 (2007).

(56) References Cited

OTHER PUBLICATIONS

Hipp et al. A novel BCMA/CD3 bispecific T-cell engager for the treatment of multiple myeloma induces selective lysis in vitro and in vivo. Leukemia 31(8):1743-1751 (2017).
Hopp et al. The effects of affinity and valency of an albumin-binding domain (ABD) on the half-life of a single-chain diabody-ABD fusion protein. Protein Eng. Des. Sel. 23(11):827-34 (2010).
Laabi et al. The BCMA gene, preferentially expressed during B lymphoid maturation, is bidirectionally transcribed. Nucleic Acids Res 22(7):1147-1154 (1994).
Müller et al. Improved Pharmacokinetics of Recombinant Bispecific Antibody Molecules by Fusion to Human Serum Albumin. J. Biol. Chem. 282(17):12650-60 (2007).
Ramadoss et al. An Anti-B Cell Maturation Antigen bispecific Antibody for Multiple Myeloma. J. Ann. Chem. Soc. 137(16):5288-91 (2015).
Smirnova et al. Identification of new splice variants of the genes BAFF and BCMA. Mol. Immunol. 45 (4):1179-83 (2008).
Spiess et al. Alternative molecular formats and therapeutic applications for bispecific antibodies. Mol. Immunol. 67(2 Pt A):95-106 (2015).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Tijink et al. Improved tumor targeting of anti-epidermal growth factor receptor nanobodies through albumin binding: taking advantage of modular Nanobody technology. Mol. Cancer Ther. 7(8):2288-97 (2008).
U.S. Appl. No. 16/159,554 Office Action dated Jun. 7, 2019.
Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).
PCT/US/2020/032985 International Search Report and Written Opinion dated Oct. 15, 2020.
U.S. Appl. No. 15/630,259 Office Action dated Sep. 30, 2020.
U.S. Appl. No. 16/159,554 Office Action dated Oct. 5, 2020.
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Schmidt et al. Cloning and Characterization of Canine Prostate-Specific Membrane Antigen. The Prostate 73:642-650 (2013).
U.S. Appl. No. 15/600,264 Office Action dated Apr. 25, 2019.
U.S. Appl. No. 15/821,498 Office Action dated May 3, 2019.
U.S. Appl. No. 15/821,530 Office Action dated Apr. 3, 2019.
U.S. Appl. No. 15/977,988 Office Action dated Mar. 26, 2019.
Co-pending U.S. Appl. No. 16/999,773, inventors Wesche; Holger et al., filed Aug. 21, 2020.
Co-pending U.S. Appl. No. 17/030,118, inventors Dubridge; Robert et al., filed Sep. 23, 2020.
Co-pending U.S. Appl. No. 17/072,370, inventors Baeuerle; Patrick et al., filed Oct. 16, 2020.
Cho et al. Targeting B Cell Maturation Antigen (BCMA) in Multiple Myeloma: Potential Uses of BCMA-Based Immunotherapy. Front Immunol 9:1821 (2018).
PCT/US2018/055659 International Search Report and Written Opinion dated Feb. 21, 2019.
PCT/US2018/055682 International Search Report and Written Opinion dated Mar. 1, 2019.
U.S. Appl. No. 15/977,968 Office Action dated Feb. 21, 2019.
Balzar et al. The biology of the 17-1A antigen (Ep-CAM). J. Mol. Med. 77:699-712 (1999).
Bluemel et al. Epitope distance to the target cell membrane and antigen size determine the potency of T cell-mediated lysis by BiTE antibodies specific for a large melanoma surface antigen. Cancer Immunol Immunother 59(8):1197-209 (2010).
Chaubal et al. Ep-CAM—a marker for the detection of disseminated tumor cells in patients suffering from SCCHN. Anticancer Res 19:2237-2242 (1999).
Dickopf et al. Format and geometries matter: Structure-based design defines the functionality of bispecific antibodies. Comput Struct Biotechnol J 18:1221-1227 (2020).
Eyvazi et al. Antibody Based EpCAM Targeted Therapy of Cancer, Review and Update. Curr Cancer Drug Targets. 18(9):857-868 (2018).
Gastl et al. Ep-CAM overexpression in breast cancer as a predictor of survival. Lancet. 356:1981-1982 (2000).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).
Koprowski et al. Colorectal carcinoma antigens detected by hybridoma antibodies. Somatic Cell Genet. 5:957-971 (1979).
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Osta et al. EpCAM is overexpressed in breast cancer and is a potential target for breast cancer gene therapy. Cancer Res 64:5818-24 (2004).
PCT/US2021/058108 International Search Report and Written Opinion dated Apr. 1, 2022.
Piyathilake et al. The expression of Ep-CAM (17-1A) in squamous cell cancers of the lung. Hum Pathol. 31:482-487 (2000).
Quak et al. Production of a monoclonal antibody (K 931) to a squamous cell carcinoma associated antigen identified as the 17-1A antigen. Hybridoma 9:377-387 (1990).
Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).
Simon et al. Epithelial glycoprotein is a member of a family of epithelial cell surface antigens homologous to nidogen, a matrix adhesion protein. PNAS USA 87:2755-2759 (1990).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
Annual Report Pursuant to Section 13 or 15(d) of the Securities Exchange Act of 1934. 2019 22-24 [online]. [Retrieved on Aug. 5, 2021]. Retrieved from website URL:https://www.annualreports.com/HostedData/AnnualReportArchive/h/NASDAQ_HARP_2018.pdf.
Brauchle et al. Characterization of a Novel FLT3 BiTE Molecule for the Treatment of Acute Myeloid Leukemia. Mol Cancer Ther 19:1875-88 (2020).
Davé et al. Fab-dsFv: A bispecific antibody format with extended serum half-life through albumin binding. MAbs 8(7):1319-1335 (2016).
Glaser et al. Novel antibody hinge regions for efficient production of CH2 domain-deleted antibodies. J. Biol. Chem. 280:41494-503 (2005).
Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Hassanzadeh-Ghassabeh et al. Nanobodies and their potential applications. Nanomedicine 8(6):1013-1026 (2013).
Huck et al. Sequence of a human immunoglobulin gamma 3 heavy chain constant region gene: comparison with the other human C gamma genes. Nucl. Acids Res. 14:1779-89 (1986).
Julian et al. Efficient affinity maturation of antibody variable domains requires co-selection of compensatory mutations to maintain thermodynamic stability. Sci Rep 7:45259 (2017).
Kim et al. Strategies and 1-17 Advancement in Antibody-Drug Conjugate Optimization for Targeted Cancer Therapeutics. Biomol Ther (Seoul) 23(6):493-509 (2015).

(56) References Cited

OTHER PUBLICATIONS

Škrlec et al. Non-immunoglobulin scaffolds: a focus on their targets. Trends in Biotechnol 33:408-418 (2015).
Krzywinska et al. CD45 Isoform Profile Identifies Natural Killer (NK) Subsets with Differential Activity. PLoS One 11(4):e0150434 (2016).
Lehmann et al. Stability engineering of anti-EGFR scFv antibodies by rational design of a lambda-to-kappa swap of the VL framework using a structure-guided approach. MAbs 7(6):1058-1071 (2015).
Leibl et al. Ovarian granulosa cell tumors frequently express EGFR (Her-1), Her-3, and Her-4: An immunohistochemical study. Gynecol Oncol 101(1):18-23 (2006).
Lin et al. Improved affinity of a chicken single-chain antibody to avian infectious bronchitis virus by site-directed mutagenesis of complementarity-determining region H3. African Journal of Biotechnology 10(79):18294-18302 (2011).
Lucchi et al. The Masking Game: Design of Activatable Antibodies and Mimetics for Selective Thera-peutics Cell Control. ACS Cent Sci 7(5):724-738 (2021).
Mason et al. CD79a: a novel marker for B-cell neoplasms in routinely processed tissue samples. Blood 86(4):1453-1459 (1995).
Mccall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
Mccarthy et al. Altering the fine specificity of an anti-Legionella single chain antibody by a single amino acid insertion. J Immunol Methods 251(1-2):137-49 (2001).
PCT/US2020/060184 International Search Report and Written Opinion dated Mar. 4, 2021.
PCT/US2021/018853 International Search Report and Written Opinion dated Jul. 8, 2021.
PCT/US2021/031790 International Search Report and Written Opinion dated Sep. 16, 2021.
Sandler et al. Nondermatologic adverse events associated with anti-EGFR therapy. Oncology (Williston Park) 20(5 Suppl 2):35-40 (2006).
Sheng et al. Novel Transgenic Mouse Model for Studying Human Serum Albumin as a Biomarker of Carcinogenic Exposure. Chem. Res. Toxicol. 29(5):797-809 (2016).
Stehle et al. Albumin-based drug carriers: comparison between serum albumins of different species on pharmacokinetics and tumor uptake of the conjugate. Anticancer Drugs. 10(8):785-90 (1999).
Stirewalt et al. The role of FLT3 in haematopoietic malignancies. Nat Rev Cancer 3:650-665 (2003).
Tan et al. Influence of the hinge region on complement activation, C1q binding, and segmental flexibility in chimeric human immunoglobulins. PNAS USA 87:162-166 (1990).
Thomas. Cetuximab: adverse event profile and recommendations for toxicity management. Clin J Oncol Nurs. 9(3):332-8 (2005).
Trail et al. Antibody drug 1-17 conjugates for treatment of breast cancer: Novel targets and diverse approaches in ADC design. Pharmacol Ther 181:126-142 (2018).
UniProtKB Accession No. A0A3M1V7M7_9EURY, Ig-like_bact domain-containing protein, Feb. 13, 2019 [online] [Retrieved on Jun. 8, 2021]. Retrieved from the internet <url:<ahref="https://www.uniprotorg/uniprot/A0A3M1V7M7.bct">https://www.uniprotorg/uniprot/A0A3M1V7M7.bct</url:.<a>.
U.S. Appl. No. 16/159,554 Office Action dated Mar. 16, 2021.
U.S. Appl. No. 16/161,986 Office Action dated Dec. 2, 2021.
U.S. Appl. No. 16/339,263 Office Action dated Jan. 11, 2022.
U.S. Appl. No. 16/489,523 Office Action dated Feb. 14, 2022.
U.S. Appl. No. 16/773,843 Office Action dated Feb. 8, 2022.

* cited by examiner

FIG. 3

| Clone | $hK_d$ | $cK_d$ | $mK_d$ |
|---|---|---|---|
| WT | 4 nM | 4.1 nM | 42.5 nM |
| 6C | 2.3 nM | 2.4 nM | 17.3 nM |
| 7A | 1.9 nM | 1.7 nM | 12.3 nM |
| 7G | 3.2 nM | 3.6 nM | 32.9 nM |
| 8H | 2.7 nM | 2.6 nM | 14.5 nM |
| 9A | 6.0nM | 7.5nM | |
| 10G | 2.2 nM | 2.3 nM | 15.7 nM |
| 6CE | 2.1 nM | 2.2 nM | 16.8 nM |
| 8HE | 2.1 nM | 2.0 nM | 16.7 nM |
| 10GE | 1.6 nM | 1.6 nM | 16.1 nM |

FIG. 4

| Anti-HSA single domain antibody variants | $T_h$ ( °C) |
|---|---|
| WT | 63 |
| 6C | 64.9 |
| 7A | 59.1 |
| 7G | 57.3 |
| 8H | 66.2 |
| 10G | 70.7 |
| 6CE | 64 |
| 8HE | 65.9 |
| 10GE | 71.1 |

FIG. 5

| Anti-HSA single domain antibody variants | % Dimer | % Monomer |
|---|---|---|
| WT | 3.9 | 96.1 |
| 6C | 6.1 | 93.9 |
| 7A | 35.1 | 64.9 |
| 7G | 22 | 78 |
| 8H | 5.5 | 94.5 |
| 10G | 1.3 | 98.7 |

SINGLE DOMAIN SERUM ALBUMIN BINDING PROTEIN

CROSS-REFERENCE

This application is a continuation of U.S. patent application Ser. No. 15/600,582, filed May 19, 2017, and claims the benefit of U.S. Provisional Application No. 62/339,682 filed May 20, 2016, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on May 18, 2017, is named 47517_703_302_SL.txt and is 22,218 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND OF THE INVENTION

Albumin is the most abundant plasma protein, is highly soluble, very stable and has an extraordinarily long circulatory half-life. Albumin can be used in a variety of ways to increase the circulatory half-life of therapeutic molecules. The present disclosure provides a single domain albumin binding protein which can be used for extending the half-life of therapeutic molecules.

SUMMARY OF THE INVENTION

Provided herein in one embodiment is a single domain serum albumin binding protein, comprising complementarity determining regions CDR1, CDR2, and CDR3, wherein (a) the amino acid sequence of CDR1 is as set forth in $GFX_1X_2X_3X_4FGMS$ (SEQ ID NO. 1), $X_1$ is threonine, arginine, lysine, serine, or proline, $X_2$ is phenylalanine or tyrosine, $X_3$ is serine, arginine or lysine, $X_4$ is serine, lysine, arginine, or alanine; (b) the amino acid sequence of CDR2 is as set forth in $SISGSGX_5X_6TLYAX_7SX_8K$ (SEQ ID NO. 2), $X_5$ is serine, arginine, threonine, or alanine, $X_6$ is aspartic acid, histidine, valine, or threonine, $X_7$ is aspartic acid, histidine, arginine, or serine, $X_8$ is valine or leucine; and (c) the amino acid sequence of CDR3 is as set forth in $GGSLX_9X_{10}$ (SEQ ID NO. 3), $X_9$ is serine, arginine, threonine, or lysine, and $X_{10}$ is arginine, lysine, valine, proline, or asparagine, wherein $X_1$, $X_2$, $X_3$, $X_4$, $X_5$, $X_6$, $X_7$, $X_8$, $X_9$, and $X_{10}$ are not simultaneously threonine, phenylalanine, serine, serine, serine, aspartic acid, aspartic acid, valine, serine, and arginine, respectively. In some embodiments, the single domain serum albumin binding protein comprises the following formula: f1-r1-f2-r2-f3-r3-f4, wherein, r1 is SEQ ID NO. 1; r2 is SEQ ID NO. 2; and r3 is SEQ ID NO. 3; and wherein $f_1$, $f_2$, $f_3$ and $f_4$ are framework residues selected so that said protein is at least eighty percent identical to the amino acid sequence set forth in SEQ ID NO. 10. In some embodiments, the single domain serum albumin binding protein comprises an amino acid sequence wherein r1 comprises SEQ ID NO. 14, SEQ ID NO. 15 or SEQ ID NO. 16. In some embodiments, the single domain serum albumin binding protein comprises an amino acid sequence wherein r2 comprises SEQ ID NO. 17, SEQ ID NO. 18, SEQ ID NO. 19, SEQ ID NO. 20, SEQ ID NO. 21, or SEQ ID NO. 22. In some embodiments, the single domain serum albumin binding protein comprises an amino acid sequence wherein r3 comprises SEQ ID NO. 23 or SEQ ID NO. 24. In some embodiments, the single domain serum albumin binding protein comprises an amino acid sequence wherein r1 comprises SEQ ID NO. 14. In some embodiments, the single domain serum albumin binding protein comprises an amino acid sequence wherein r1 comprises SEQ ID NO. 15, r2 comprises SEQ ID NO. 17, and r3 comprises SEQ ID NO.23. In some embodiments, the single domain serum albumin binding protein comprises an amino acid sequence wherein r1 comprises SEQ ID NO. 16, and r3 comprises SEQ ID NO. 23. In some embodiments, the single domain serum albumin binding protein comprises an amino acid sequence wherein r1 comprises SEQ ID NO. 15, and r2 comprises SEQ ID NO. 18. In some embodiments, the single domain serum albumin binding protein comprises an amino acid sequence wherein r1 comprises SEQ ID NO. 14, and r3 comprises SEQ ID NO. 23. In some embodiments, the single domain serum albumin binding protein comprises an amino acid sequence wherein r1 comprises SEQ ID NO. 15, r2 comprises SEQ ID NO. 19 and r3 comprises SEQ ID NO. 24. In some embodiments, the single domain serum albumin binding protein comprises an amino acid sequence wherein r1 comprises SEQ ID NO. 14, and r2 comprises SEQ ID NO. 20. In some embodiments, the single domain serum albumin binding protein comprises an amino acid sequence wherein r1 comprises SEQ ID NO. 15, and r2 comprises SEQ ID NO. 21. In some embodiments, the single domain serum albumin binding protein comprises an amino acid sequence wherein r1 comprises SEQ ID NO. 15, r2 comprises SEQ ID NO. 22, and r3 comprises SEQ ID NO. 24. In some embodiments, the single domain serum albumin binding protein has an amino acid sequence selected from SEQ ID NO. 4, SEQ ID NO. 5, SEQ ID NO. 6, SEQ ID NO. 7, SEQ ID NO. 8, SEQ ID NO. 9, SEQ ID NO. 25, SEQ ID NO. 26, and SEQ ID NO. 27. In some embodiments, the single domain serum albumin binding protein comprises the amino acid sequence set forth as SEQ ID NO. 4. In some embodiments, the single domain serum albumin binding protein comprises the amino acid sequence set forth as SEQ ID NO. 7. In some embodiments, the single domain serum albumin binding protein comprises the amino acid sequence set forth as SEQ ID NO. 9. In some embodiments, the single domain serum albumin binding protein comprises the amino acid sequence set forth as SEQ ID NO. 26. In some embodiments, the single domain serum albumin binding protein comprises the amino acid sequence set forth as SEQ ID NO. 27.

In some embodiments, the single domain serum albumin binding protein binds to serum albumin selected from human serum albumin, cynomolgus serum albumin, and mouse serum albumin. In some embodiments, the single domain serum albumin binding protein binds to human serum albumin and cynomolgus serum albumin with comparable binding affinity (Kd).

In some embodiments, the single domain serum albumin binding protein binds to mouse serum albumin with a binding affinity (Kd) that is about 1.5 fold to about 20 fold weaker than the binding affinity (Kd) of said protein towards human and cynomolgus serum albumin. In some embodiments, the single domain serum albumin binding protein binds to human serum albumin with a human Kd (hKd)

between about 1 nM and about 100 nM and to cynomolgus serum albumin with a cynomolgus Kd (cKd) between 1 nM and 100 nM. In some embodiments, the hKd and the cKd of the single domain serum albumin binding protein are between 1 nM and about 5 nM, or about 5 nM and about 10 nM. In some embodiments, the hKd and cKd of the single domain serum albumin binding protein are between about 1 nM and about 2 nM, about 2 nM and about 3 nM, about 3 nM and about 4 nM, about 4 nM and about 5 nM, about 5 nM and about 6 nM, about 6 nM and about 7 nM, about 7 nM and about 8 nM, about 8 nM and about 9 nM, or about 9 nM and about 10 nM. In some embodiments, the ratio between the hKd and cKd (hKd:cKd) of the single domain serum albumin binding protein ranges from about 20:1 to about 1:2.

In some embodiments, the single domain serum albumin binding protein comprises the amino acid sequence set forth as SEQ ID NO. 4, and wherein the hKd and the cKd are between about 1 nM and about 5 nM. In some embodiments, the single domain serum albumin binding protein comprises the amino acid sequence set forth as SEQ ID NO. 5, and wherein the hKd and the cKd are between about 1 nM and about 5 nM. In some embodiments, the single domain serum albumin binding protein comprises the amino acid sequence set forth as SEQ ID NO. 6, and wherein the hKd and the cKd are between about 1 nM and about 5 nM. In some embodiments, the single domain serum albumin binding protein comprises the amino acid sequence set forth as SEQ ID NO. 7, and wherein the hKd and the cKd are between about 1 nM and about 5 nM. In some embodiments, the single domain serum albumin binding protein comprises the amino acid sequence set forth as SEQ ID NO. 8, and wherein the hKd and the cKd are between about 5 nM and about 10 nM. In some embodiments, the single domain serum albumin binding protein comprises the amino acid sequence set forth as SEQ ID NO. 9, and wherein the hKd and the cKd are between about 1 nM and about 5 nM. In some embodiments, the single domain serum albumin binding protein comprises the amino acid sequence set forth as SEQ ID NO. 22, and wherein the hKd and the cKd are between about 1 nM and about 5 nM. In some embodiments, the single domain serum albumin binding protein comprises the amino acid sequence set forth as SEQ ID NO. 23, and wherein the hKd and the cKd are between about 1 nM and about 5 nM. In some embodiments, the single domain serum albumin binding protein comprises the amino acid sequence set forth as SEQ ID NO. 24, and wherein the hKd and the cKd are between about 1 nM and about 5 nM.

In some embodiments, the single domain serum albumin binding protein comprises elimination half-time of at least 12 hours, at least 20 hours, at least 25 hours, at least 30 hours, at least 35 hours, at least 40 hours, at least 45 hours, at least 50 hours, or at least 100 hours.

In another embodiment is provided a single domain serum albumin binding protein comprising CDR1, CDR2, and CDR3, comprising the sequence set forth as SEQ ID NO. 10 wherein one or more amino acid residues selected from amino acid positions 28, 29, 30, or 31 of CDR1; positions 56, 57, 62, or 64 of CDR2; and positions 103, and 104 of CDR3 are substituted, wherein amino acid position 28 is substituted with arginine, lysine, serine, or proline, amino acid position 29 is substituted with tyrosine, amino acid position 30 is substituted with arginine or lysine, amino acid position 31 is substituted with lysine, arginine, or alanine, amino acid position 56 is substituted with arginine, threonine, or alanine, amino acid position 57 is substituted with histidine, valine, or threonine, amino acid position 62 is substituted with histidine, arginine, glutamic acid, or serine, amino acid position 64 is substituted with leucine, amino acid position 103 is substituted with arginine, threonine, or lysine, amino acid position 104 is substituted with lysine, valine, proline, or asparagine. In some embodiments, the single domain serum albumin binding comprises one or more additional substitutions in amino acid positions other than positions 28, 29, 30, 31, 56, 57, 62, 64, 103, and 104. In some embodiments, the single domain serum albumin binding protein comprises a substitution in position 29. In some embodiments, the single domain serum albumin binding protein comprises a substitution in position 31. In some embodiments, the single domain serum albumin binding protein comprises a substitution in position 56. In some embodiments, the single domain serum albumin binding protein comprises a substitution in position 62. In some embodiments, the single domain serum albumin binding protein comprises a substitution in position 64. In some embodiments, the single domain serum albumin binding protein comprises a substitution in position 104. In some embodiments, the single domain serum albumin binding protein comprises substitutions in amino acid positions 3 land 62. In some embodiments, the single domain serum albumin binding protein comprises a amino acid sequence wherein position 31 is substituted with arginine. In some embodiments, the single domain serum albumin binding protein comprises an amino acid sequence wherein position 31 is substituted with arginine and amino acid position 62 is substituted with glutamic acid. In some embodiments, the single domain serum albumin binding protein comprises substitutions in amino acid positions 31, 56, 64, and 104. In some embodiments, the single domain serum albumin binding protein comprises an amino acid sequence wherein position 31 is substituted with lysine, amino acid position 56 is substituted with alanine, amino acid position 64 is substituted with leucine, and amino acid position 104 is substituted with lysine. In some embodiments, the single domain serum albumin binding protein comprises substitutions in amino acid positions 29 and 104. In some embodiments, the single domain serum albumin binding protein comprises an amino acid sequence wherein amino acid position 29 is substituted with tyrosine, and amino acid position 104 is substituted with lysine. In some embodiments, the single domain serum albumin binding protein comprises substitutions in amino acid positions 31 and 56. In some embodiments, the single domain serum albumin binding protein comprises an amino acid sequence wherein amino acid position 31 is substituted with lysine, and amino acid position 56 is substituted with threonine. In some embodiments, the single domain serum albumin binding protein comprises substitutions in amino acid positions 31, 56, and 62. In some embodiments, the single domain serum albumin binding protein comprises an amino acid sequence wherein amino acid position 31 is substituted with lysine, amino acid position 56 is substituted with threonine, and amino acid position 62 is substituted with glutamic acid. In some embodiments, the single domain serum albumin binding protein comprises substitutions in amino acid positions 31 and 104. In some embodiments, the single domain serum albumin binding protein comprises an amino acid sequence wherein amino acid position 31 is substituted with arginine, and amino acid position 104 is substituted with lysine. In some embodiments, the single domain serum albumin binding protein comprises substitutions in amino acid positions 31, 56, and 104. In some embodiments, the single domain serum albumin binding protein comprises an amino acid sequence wherein amino acid position 31 is substituted with lysine, amino acid position 56 is substituted with arginine, and amino acid position 104 is substituted with valine. In some embodiments, the single domain serum albumin binding protein comprises substitutions in amino acid positions 31, 56, 62, and 104. In some embodiments, the single domain serum albumin binding protein comprises an amino acid sequence wherein amino acid position 31 is substituted with lysine, amino acid position 56 is substituted with arginine, amino acid position 62 is substituted with glutamic acid, and amino acid position 104 is substituted with valine. In some embodiments, the single domain serum albumin binding protein comprises an amino acid sequence wherein amino acid position 31 is substituted with arginine, and the hKd and the cKd of the single domain serum albumin binding protein are between about 1 nM and about 5 nM. In some embodiments, the single domain serum albumin binding protein comprises an amino acid sequence wherein amino acid position 31 is substituted with arginine, amino acid position 62 is substituted with glutamic acid, and the hKd and the cKd of the single domain serum albumin binding protein are between about 1 nM and about 5 nM. In some embodiments, the single domain serum albumin binding protein comprises an amino acid sequence wherein amino acid position 31 is substituted with lysine, amino acid position 56 is substituted with alanine, amino acid position 64 is substituted with leucine, amino acid position 104 is substituted with lysine, and wherein the hKd and the cKd of the single domain serum albumin binding protein are between about 1 nM and about 5 nM. In some embodiments, the single domain serum albumin binding protein comprises an amino acid sequence wherein amino acid position 29 is substituted with tyrosine, amino acid position 104 is substituted with lysine, and wherein the hKd and the cKd are between about 1 nM and about 5 nM. In some embodiments, the single domain serum albumin binding protein comprises an amino acid sequence wherein amino acid position 31 is substituted with lysine, amino acid position 56 is substituted with threonine, and wherein the hKd and the cKd of the single domain serum albumin binding protein are between about 1 nM and about 5 nM. In some embodiments, the single domain serum albumin comprises an amino acid sequence wherein amino acid position 31 is substituted with lysine, amino acid position 56 is substituted with threonine, and amino acid position 62 is substituted with glutamic acid, and wherein the hKd and the cKd are between about 1 nM and about 5 nM. In some embodiments, the single domain serum albumin binding protein comprises an amino acid sequence wherein amino acid position 31 is substituted with arginine, amino acid position 104 is substituted with lysine, and wherein the hKd and the cKd of the single domain serum albumin binding protein are between about 5 nM and about 10 nM. In some embodiments, the single domain serum albumin binding protein comprises an amino acid sequence wherein amino acid position 31 is substituted with lysine, amino acid position 56 is substituted with arginine, amino acid position 104 is substituted with valine, and wherein the hKd and the cKd of the single domain serum albumin binding protein are between about 1 nM and about 5 nM. In some embodiments, the single domain serum albumin binding protein comprises an amino acid sequence wherein amino acid position 31 is substituted with lysine, amino acid position 56 is substituted with arginine, amino acid position 62 is substituted with glutamic acid, and amino acid position 104 is substituted with valine, and wherein the hKd and the cKd of the single domain serum albumin binding protein are between about 1 nM and about 5 nM.

Provided herein in another embodiment is a single domain serum albumin binding protein comprising at least one mutation in CDR1, CDR2 or CDR3, wherein CDR1 comprises the sequence as set forth is SEQ ID NO: 11, CDR2 comprises the sequence as set forth in SEQ ID NO: 12, CDR3 comprises the sequence as set forth in SEQ ID NO. 13, and wherein the at least one mutation is not in amino acid positions 1, 2, 7, 8, 9, or 10 of SEQ ID NO: 11, positions 1, 3, 6, 10, or 11 of SEQ ID NO: 12, or positions 1 or 2 of SEQ ID NO: 13. In some embodiments, the single domain serum albumin binding protein comprises at least one mutation in amino acid positions selected from positions 3, 4, 5, and 6 of CDR1 (SEQ ID NO: 11), amino acid positions 7, 8, 13, and 15 of CDR2 (SEQ ID NO: 12), and amino acid positions 5 and 6 of CDR3 (SEQ ID NO: 13). In some embodiments, the single domain serum albumin binding protein comprises one or more additional substitutions in amino acid positions other than 3, 4, 5, and 6 of CDR1 (SEQ ID NO: 11), amino acid positions 7, 8, 13, and 15 of CDR2 (SEQ ID NO: 12), and amino acid positions 5 and 6 of CDR3 (SEQ ID NO: 13). In some embodiments, the single domain serum albumin binding protein comprises a mutation in amino acid position 6 of CDR 1 (SEQ ID NO: 11). In some embodiments, the single domain serum albumin binding protein comprises a mutation in amino acid position 6 of CDR 1 (SEQ ID NO:11), and amino acid position 13 of CDR2 (SEQ ID NO: 12). In some embodiments, the single domain serum albumin binding protein comprises mutations in amino acid position 6 of (SEQ ID NO: 11), amino acid positions 7 and 15 of CDR2 (SEQ ID NO: 12), and amino acid position 6 of CDR3 (SEQ ID NO: 13). In some embodiments, the single domain serum albumin binding protein comprises mutations in amino acid position 4 of CDR1 (SEQ ID NO:11), and amino acid position 6 of CDR3 (SEQ ID NO: 13). In some embodiments, the single domain serum albumin binding protein comprises mutations in amino acid position 6 of CDR 1 (SEQ ID NO:11), and amino acid position 7 of CDR2 (SEQ ID NO: 12). In some embodiments, the single domain serum albumin binding protein comprises mutations in amino acid position 6 of CDR 1 (SEQ ID NO: 11), and amino acid positions 7 and 13 of CDR2 (SEQ ID NO: 12). In some embodiments, the single domain serum albumin binding protein comprises mutations in amino acid position 6 of CDR1 (SEQ ID NO:11), and amino acid position 6 of CDR3 (SEQ ID NO: 13). In some embodiments, the single domain serum albumin binding protein comprises mutations in amino acid position 6 of CDR1 (SEQ ID NO: 11), amino acid position 7 of CDR2 (SEQ ID NO: 12), and amino acid position 6 of CDR3 (SEQ ID NO: 13). In some embodiments, the single domain serum albumin binding protein comprises mutations in amino acid position 6 of CDR1 (SEQ ID NO: 11), amino acid positions 7 and 13 of CDR2 (SEQ ID NO: 12), and amino acid position 6 of CDR3 (SEQ ID NO: 13). In some embodiments, the single domain serum albumin binding protein comprises an amino acid sequence wherein amino acid position 6 of CDR1 (SEQ ID NO: 11) is mutated to arginine, and wherein the hKd and the cKd of the single domain serum albumin binding protein are between about 1 nM and about 5 nM. In some embodiments, the single domain serum albumin binding protein comprises an amino acid sequence wherein amino acid position 6 of CDR1 (SEQ ID NO: 11) is mutated to arginine, and amino acid position 13 of CDR2 (SEQ ID NO: 12) is mutated to glutamic acid, and wherein the hKd and the cKd of the single domain serum albumin binding protein are between about 1 nM and about 5 nM. In some embodiments, the single domain serum albumin binding protein comprises an amino acid sequence wherein amino acid position 6 is of CDR 1 (SEQ ID NO: 11) is mutated to lysine, amino acid positions 7 and 15 of CDR2 (SEQ ID NO: 12) are mutated to alanine and leucine, respectively, amino acid position 6 of CDR3 (SEQ ID NO: 13) is mutated to lysine, and wherein the hKd and the cKd of the single domain serum albumin binding protein are between about 1 nM and about 5 nM. In some embodiments, the single domain serum albumin binding protein comprises an amino acid sequence wherein amino acid position 4 of CDR1 (SEQ ID NO: 11) is mutated to tyrosine, and amino acid position 6 of CDR3 (SEQ ID NO: 13) is mutated to lysine, and wherein the hKd and the cKd of the single domain serum albumin binding protein are between about 1 nM and about 5 nM. In some embodiments, the single domain serum albumin binding protein comprises an amino acid sequence wherein amino acid position 6 of CDR 1 (SEQ ID NO: 11) is mutated to lysine, amino acid position 7 of CDR2 (SEQ ID NO: 12) is mutated to threonine, and wherein the hKd and the cKd of the single domain serum albumin binding protein are between about 1 nM and about 5 nM. In some embodiments, the single domain serum albumin binding protein comprises an amino acid sequence wherein amino acid position 6 of CDR 1 (SEQ ID NO: 11) is mutated to lysine, amino acid positions 7 and 13 of CDR2 (SEQ ID NO: 12) are mutated to threonine and glutamic acid, respectively, and wherein the hKd and the cKd of the single domain serum albumin binding protein are between about 1 nM and about 5 nM. In some embodiments, the single domain serum albumin binding protein comprises an amino acid sequence wherein amino acid position 6 of CDR1 (SEQ ID NO:11) is mutated to arginine, amino acid position 6 of CDR3 (SEQ ID NO: 12) is mutated to lysine, and wherein the hKd and the cKd of the single domain serum albumin binding protein are between about 5 nM and about 10 nM. In some embodiments, the single domain serum albumin binding protein comprises an amino acid sequence wherein amino acid position 6 of CDR 1 (SEQ ID NO: 11) is mutated to lysine, amino acid position 7 of CDR2 (SEQ ID NO: 12) is mutated to arginine, amino acid position 6 of CDR3 (SEQ ID NO: 13) is mutated to valine, and wherein the hKd and the cKd of the single domain serum albumin binding protein are between about 1 nM and about 5 nM. In some embodiments, the single domain serum albumin binding protein comprises an amino acid sequence wherein amino acid position 6 of CDR 1 (SEQ ID NO: 11) is mutated to lysine, amino acid positions 7 and 13 of CDR2 (SEQ ID NO: 12) is mutated to arginine and glutamic acid, respectively, and amino acid position 6 of CDR3 (SEQ ID NO: 13) is mutated to valine, and wherein the hKd and the cKd of the single domain serum albumin binding protein are between about 1 nM and about 5 nM.

Provided herein in another embodiment, a polynucleotide encoding a single domain serum albumin binding protein according to the present disclosure. A further embodiment describes a vector comprising the polynucleotide as disclosed herein. Another embodiment describes a host cell transformed with the vector according to the present disclosure. In one embodiment is provided a pharmaceutical composition comprising (i) a single domain serum albumin binding protein according to the present disclosure, a polynucleotide according to the present disclosure, a vector according to the present disclosure or a host cell according to the present disclosure, and (ii) a pharmaceutically acceptable carrier.

Described herein in another embodiment, is a process for the production of a single domain serum albumin binding protein according to the present disclosure, said process comprising culturing a host transformed or transfected with a vector comprising a nucleic acid sequence encoding a single domain serum albumin binding protein as described herein under conditions allowing the expression of the serum albumin binding protein and recovering and purifying the produced protein from the culture.

Further described is a method for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease comprising the administration of the single domain serum albumin binding protein according to the present disclosure, to a subject in need thereof. In some embodiments, the subject is human. In some embodiments, the method further comprises administration of an agent in combination with the single domain serum albumin binding protein according to the present disclosure.

In another embodiment is described a multispecific binding protein comprising the single domain serum albumin binding protein according to the present disclosure. In another embodiment is described an antibody comprising the single domain serum albumin binding protein according to the present disclosure.

A further embodiment describes a multispecific antibody, a bispecific antibody, an sdAb, a variable heavy domain, a peptide, or a ligand, comprising the single domain serum albumin binding protein according to the present disclosure. In one embodiment is provided an antibody comprising the single domain serum albumin binding protein according to the present disclosure, wherein said antibody is a single domain antibody. In some embodiments, the single domain antibody is derived from a heavy chain variable region of IgG.

One embodiment describes a multispecific binding protein or antibody comprising the single domain serum albumin binding protein according to the present disclosure and a CD3 binding domain. In one embodiment is described a method for the treatment or amelioration of a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease comprising administration of the multispecific antibody according to the present disclosure, to a subject in need thereof.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 provides the binding affinity profiles of nine clones selected for more precise Kd determinations using purified sdAbs.

FIG. 4 illustrates the temperature of hydrophobic exposure ($T_h$° C.) for several anti-HSA sdAb variants.

FIG. 5 illustrates the propensity of several anti-HSA sdAb variants to form dimer versus monomer at low pH.

DETAILED DESCRIPTION OF THE INVENTION

Figure 1:
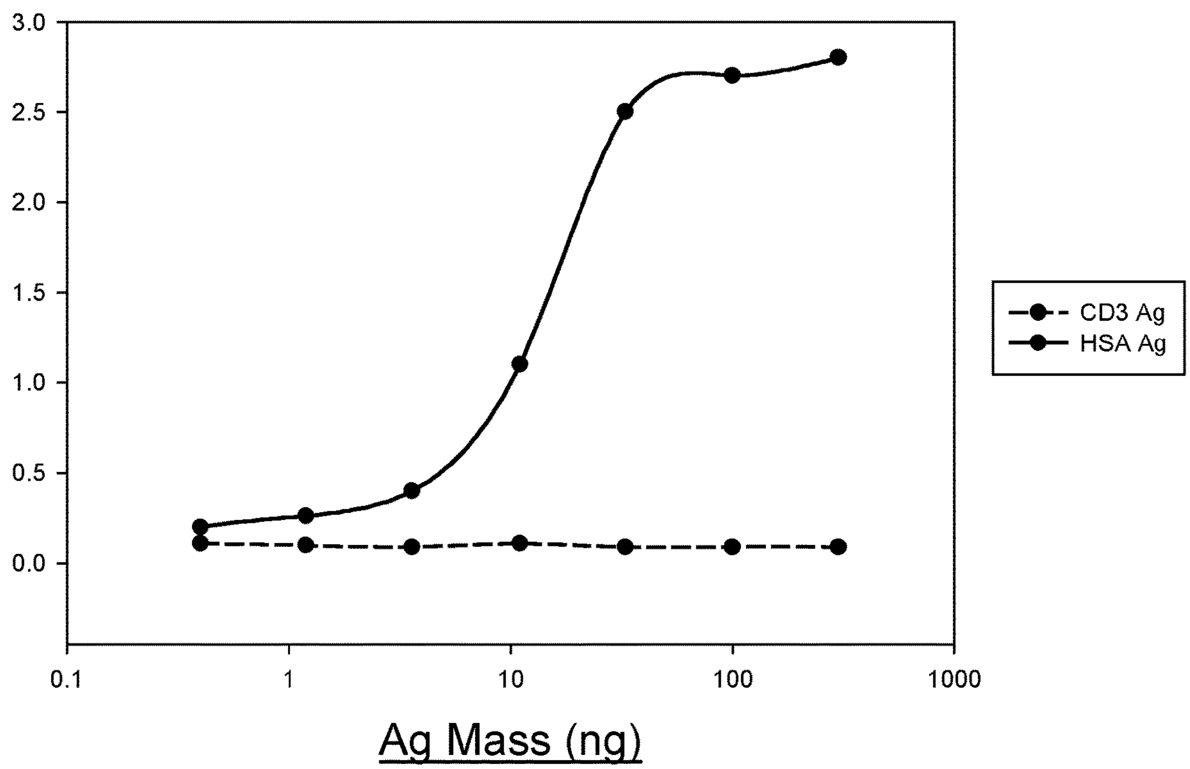
FIG. 1 illustrates the specific binding of parental anti-HSA phage as determined by ELISA titration to an HSA antigen and a CD3 antigen.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. "Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence. It is not intended that CDRs of the present disclosure necessarily correspond to the Kabat numbering convention.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in *Goodman and Gillman's The Pharmaceutical Basis of Therapeutics* 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, $t_{1/2}$ the time required for 50% completion of the process. The units of these two constants are $time^{-1}$ and time, respectively. A first-order rate constant and the half-time of the reaction are simply related ($k \times t_{1/2}=0.693$) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within +2-fold of each other. If two or more proteins are indicated to have comparable binding affinities towards single binding target, then the Kd values for binding of the respective proteins towards said single binding target, are within +2-fold of each other. If a protein is indicated to bind two or more targets with comparable binding affinities, then the Kd values for binding of said protein to the two or more targets are within +2-fold of each other. In general, a higher Kd value corresponds to a weaker binding. In some embodiments, the "Kd" is measured by a radiolabeled antigen binding assay (RIA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the Octet® Systems (Pall Life Sciences).

Described herein are single domain serum albumin binding proteins, pharmaceutical compositions as well as nucleic acids, recombinant expression vectors, and host cells for making such single domain serum albumin binding proteins. Also provided are methods of using the disclosed single domain serum albumin binding proteins in the prevention, and/or treatment of diseases, conditions and disorders. The single domain serum albumin binding proteins are capable specifically binding to serum albumin. In some embodiments, the single domain serum albumin binding proteins include additional domains, such as a CD3 binding domain, as well as binding domains for other target antigens.

Single Domain Serum Albumin Binding Protein

Contemplated herein are single domain serum albumin binding proteins. Serum albumin is produced by the liver, occurs dissolved in blood plasma and is the most abundant blood protein in mammals. Albumin is essential for maintaining the oncotic pressure needed for proper distribution of body fluids between blood vessels and body tissues; without albumin, the high pressure in the blood vessels would force more fluids out into the tissues. It also acts as a plasma carrier by non-specifically binding several hydrophobic steroid hormones and as a transport protein for hemin and fatty acids. Human serum albumin (HSA) (molecular mass ~67 kDa) is the most abundant protein in plasma, present at about 50 mg/ml (600 μM), and has a half-life of around 20 days in humans. HSA serves to maintain plasma pH, contributes to colloidal blood pressure, functions as carrier of many metabolites and fatty acids, and serves as a major drug transport protein in plasma. In some embodiments, the single domain serum albumin binding proteins bind to HSA. In some embodiments, the single domain serum albumin binding proteins bind to serum albumin protein from cynomolgus monkeys. In some embodiments, the single domain serum albumin binding proteins bind to HSA and serum albumin protein from cynomolgus monkeys. In some embodiments, the single domain serum albumin binding proteins also bind to mouse serum albumin protein. In some embodiments, the binding affinity towards mouse serum albumin is about 1.5-fold to about 20-fold weaker than that towards human or cynomolgus serum albumin.

Noncovalent association with albumin extends the elimination half-time of short lived proteins. For example, a recombinant fusion of an albumin binding domain to a Fab fragment resulted in a decrease in in vivo clearance by 25- and 58-fold and a half-life extension of 26- and 37-fold when administered intravenously to mice and rabbits respectively as compared to the administration of the Fab fragment alone. In another example, when insulin is acylated with fatty acids to promote association with albumin, a protracted effect was observed when injected subcutaneously in rabbits or pigs. Together, these studies demonstrate a linkage between albumin binding and prolonged action/serum half-life.

In some embodiments, the single-domain serum albumin binding proteins described herein is a single domain antibody such as a heavy chain variable domain (VH), a variable domain (VHH) of camelid derived sdAb, peptide, ligand or small molecule entity specific for serum albumin. In some embodiments, the single-domain serum albumin binding proteins described herein is a single domain antibody such as a heavy chain variable domain (VH), a variable domain (VHH) of camelid derived sdAb, peptide, ligand or small molecule entity specific for HSA. In some embodiments, the serum albumin binding domain of a single domain serum albumin binding protein described herein is any domain that binds to serum albumin including but not limited to domains from a monoclonal antibody, a polyclonal antibody, a recombinant antibody, a human antibody, a humanized antibody. In certain embodiments, the serum albumin binding domain is a single-domain antibody. In other embodiments, the serum albumin binding domain is a peptide. In further embodiments, the serum albumin binding domain is a small molecule. It is contemplated that the single domain serum albumin binding protein is fairly small and no more than 25 kD, no more than 20 kD, no more than 15 kD, or no more than 10 kD in some embodiments. In certain instances, the single domain serum albumin binding protein binding is 5 kD or less if it is a peptide or small molecule entity.

In some embodiments, the single domain serum albumin binding protein described herein is a half-life extension domain which provides for altered pharmacodynamics and pharmacokinetics of the single domain serum albumin binding protein itself. As above, the half-life extension domain extends the elimination half-time. The half-life extension domain also alters pharmacodynamic properties including alteration of tissue distribution, penetration, and diffusion of the single domain serum albumin binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the single domain serum albumin binding protein, resulting in reduced side effects, such as reduced non-tumor cell cytotoxicity.

Further, the binding affinity of the single domain serum albumin binding protein towards its binding target can be selected so as to target a specific elimination half-time in a particular single domain serum albumin binding protein.

Thus, in some embodiments, the single domain serum albumin binding protein has a high binding affinity towards its binding target. In other embodiments, the single domain serum albumin binding protein has a medium binding affinity towards its binding target. In yet other embodiments, the single domain serum albumin binding protein has a low or marginal binding affinity towards its binding target. Exemplary binding affinities include $K_D$ of 10 nM or less (high), between 10 nM and 100 nM (medium), and greater than 100 nM (low). As above, binding affinities of the single domain serum albumin binding proteins towards binding targets are determined by known methods such as Surface Plasmon Resonance (SPR).

In certain embodiments, the single domain serum albumin binding protein disclosed herein binds to HSA with a human Kd (hKd). In certain embodiments, the single domain serum albumin binding protein disclosed herein binds to cynomolgus monkey serum albumin with a cyno Kd (cKd). In certain embodiments, the single domain serum albumin binding protein disclosed herein binds to cynomolgus monkey serum albumin with a cyno Kd (cKd) and to HSA with a human Kd (hKd). In some embodiments, the hKd ranges between 1 nM and 100 nM. In some embodiments, the hKd ranges between 1 nM and 10 nM. In some embodiments, the cKd ranges between 1 nM and 100 nM. In some embodiments, the cKd ranges between 1 nM and 10 nM. In some embodiments, the hKd and the cKd range between about 1 nM and about 5 nM or between about 5 nM and 10 nM. In some embodiments, the single domain serum albumin binding protein binds to serum albumin selected from human serum albumin, cynomolgus serum albumin, and mouse serum albumin. In some embodiments, the single domain serum albumin binding protein binds to human serum albumin, cynomolgus serum albumin, and mouse serum albumin with comparable binding affinity (Kd). In some embodiments, the single domain serum albumin binding protein binds to human serum albumin with a human Kd (hKd) between about 1 nM and about 10 nM and to cynomolgus serum albumin with a cynomolgus Kd (cKd) between 1 nM and 10 nM. In some embodiments, the single domain serum albumin binding protein binds to mouse serum albumin with a mouse Kd (mKd) between about 10 nM and about 50 nM.

In some embodiments, the hKd is about 1.5 nM, about 1.6 nM, about 1.7 nM, about 1.8 nM, about 1.9 nM, about 2 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, 3.1 nM, about 3.2 nM, about 3.3. nM, about 3.4 nM, about 3.5 nM, about 3.6 nM, about 3.7 nM, about 3.8 nM, about 3.9 nM, about 4 nM, about 4.5 nM, about 5 nM, about 6, about 6.5 nM, about 7 nM, about 7.5 nM, about 8 nM, about 8.5 nM, about 9.0 nM, about 9.5 nM, or about 10 nM.

In some embodiments, the cKd is about 1.5 nM, about 1.6 nM, about 1.7 nM, about 1.8 nM, about 1.9 nM, about 2 nM, about 2.1 nM, about 2.2 nM, about 2.3 nM, about 2.4 nM, about 2.5 nM, about 2.6 nM, about 2.7 nM, about 2.8 nM, about 2.9 nM, about 3 nM, 3.1 nM, about 3.2 nM, about 3.3. nM, about 3.4 nM, about 3.5 nM, about 3.6 nM, about 3.7 nM, about 3.8 nM, about 3.9 nM, about 4 nM, about 4.5 nM, about 5 nM, about 6, about 6.5 nM, about 7 nM, about 7.5 nM, about 8 nM, about 8.5 nM, about 9.0 nM, about 9.5 nM, or about 10 nM.

In some embodiments, the mKd is about 10 nM, about 11 nM, about 12 nM, about 13 nM, about 14 nM, about 15 nM, about 16 nM, about 17 nM, about 18 nM, about 19 nM, about 20 nM, about 21 nM, about 22 nM, about 23 nM, about 24 nM, about 25 nM, about 26 nM, about 27. nM, about 28 nM, about 29 nM, about 30 nM, about 31 nM, about 32 nM, about 33 nM, about 34 nM, about 35 nM, about 36 nM, about 37, about 38 nM, about 39 nM, about 40 nM, about 41 nM, about 42 nM, about 43 nM, about 44 nM, about 45 nM, about 46 nM, about 47 nM, about 48 nM, or about 50 nM.

In some embodiments, the single domain serum albumin binding protein has an amino acid sequence selected from SEQ ID NO. 4, SEQ ID NO. 5, SEQ ID NO. 6, SEQ ID NO. 7, SEQ ID NO. 8, SEQ ID NO. 9, SEQ ID NO. 25, SEQ ID NO. 26, and SEQ ID NO. 27.

In some embodiments, the single domain serum albumin binding protein has the amino acid sequence set forth as SEQ ID NO. 4, and the hKd and the cKd are between about 1 nM and about 5 nM. In some embodiments, the single domain serum albumin binding protein has the amino acid sequence set forth as SEQ ID NO. 4, and the hKd is about 2.3 nM and the cKd is about 2.4 nM. In some embodiments, the single domain serum albumin binding protein has the amino acid sequence set forth as SEQ ID NO. 25, and the hKd and the cKd are between about 1 nM and about 5 nM. In some embodiments, the single domain serum albumin binding protein has the amino acid sequence set forth as SEQ ID NO. 25, and the hKd is about 2.1 nM and the cKd is about 2.2 nM. In some embodiments, the single domain serum albumin binding protein has the amino acid sequence set forth as SEQ ID NO. 5, and the hKd and the cKd are between about 1 nM and about 5 nM. In some embodiments, the single domain serum albumin binding protein has the amino acid sequence set forth as SEQ ID NO. 5, and the hKd is about 1.9 nM and the cKd is about 1.7 nM. In some embodiments, the single domain serum albumin binding protein has the amino acid sequence set forth as SEQ ID NO. 6, and the hKd and the cKd are between about 1 nM and about 5 nM. In some embodiments, the single domain serum albumin binding protein has the amino acid sequence set forth as SEQ ID NO. 6, and the hKd is about 3.2 nM and the cKd is about 3.6 nM. In some embodiments, the single domain serum albumin binding protein has the amino acid sequence set forth as SEQ ID NO. 7, and the hKd and the cKd are between about 1 nM and about 5 nM. In some embodiments, the single domain serum albumin binding protein has the amino acid sequence set forth as SEQ ID NO. 7, and the hKd is about 2.7 nM and the cKd is about 2.6 nM. In some embodiments, the single domain serum albumin binding protein has the amino acid sequence set forth as SEQ ID NO. 26, and the hKd and the cKd are between about 1 nM and about 5 nM. In some embodiments, the single domain serum albumin binding protein has the amino acid sequence set forth as SEQ ID NO. 26, and the hKd is about 2.1 nM and the cKd is about 2 nM. In some embodiments, the single domain serum albumin binding protein has the amino acid sequence set forth as SEQ ID NO. 8, and the hKd and the cKd are between about 5 nM and about 10 nM. In some embodiments, the single domain serum albumin binding protein has the amino acid sequence set forth as SEQ ID NO. 8, and the hKd is about 6 nM and the cKd is about 7.5 nM. In some embodiments, the single domain serum albumin binding protein has the amino acid sequence set forth as SEQ ID NO. 9, and wherein the hKd and the cKd are between about 1 nM and about 5 nM. In some embodiments, the single domain serum albumin binding protein has the amino acid sequence set forth as SEQ ID NO. 9, and wherein the hKd is about 2.2 nM and the cKd is about 2.3 nM. In some embodiments, the single domain serum albumin binding protein has the amino acid sequence set forth as SEQ ID NO. 27 and wherein the hKd and the cKd are between about 1 nM and about 5 nM. In some embodiments, the single domain serum albumin binding protein has the amino acid sequence set forth as SEQ ID NO. 27 and wherein the hKd is about 1.6 nM and the cKd is about 1.6 nM.

In some embodiments, the single domain serum albumin binding protein has the amino acid sequence set forth as SEQ ID NO. 4 and has a mKd of about 17 nM. In some embodiments, the single domain serum albumin binding protein has the amino acid sequence set forth as SEQ ID NO. 5 and has a mKd of about 12 nM. In some embodiments, the single domain serum albumin binding protein has the amino acid sequence set forth as SEQ ID NO. 6 and has a mKd of about 33 nM. In some embodiments, the single domain serum albumin binding protein has the amino acid sequence set forth as SEQ ID NO. 7 and has a mKd of about 14 nM. In some embodiments, the single domain serum albumin binding protein has the amino acid sequence set forth as SEQ ID NO. 9 and has a mKd of about 16 nM. In some embodiments, the single domain serum albumin binding protein has the amino acid sequence set forth as SEQ ID NO. 25 and has a mKd of about 17 nM. In some embodiments, the single domain serum albumin binding protein has the amino acid sequence set forth as SEQ ID NO. 26 and has a mKd of about 17 nM. In some embodiments, the single domain serum albumin binding protein has the amino acid sequence set forth as SEQ ID NO. 27 and has a mKd of about 16 nM.

In some embodiments, the ratio between the hKd and cKd (hKd: cKd) ranges from about 20:1 to about 1:2.

In some embodiments, the single domain serum albumin binding protein has an elimination half-time of at least 1 hour, at least 2 hours, at least 4 hours, at least 6 hours, at least 12 hours, at least 20 hours, at least 25 hours, at least 30 hours, at least 35 hours, at least 40 hours, at least 45 hours, at least 50 hours, or at least 100 hours.

CD3 Binding Domain

The specificity of the response of T cells is mediated by the recognition of antigen (displayed in context of a major histocompatibility complex, MHC) by the T cell receptor complex. As part of the T cell receptor complex, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the T cell receptor (TCR) as well as and CD3ζ (zeta) altogether to comprise the T cell receptor complex. Clustering of CD3 on T cells, such as by immobilized anti-CD3 antibodies leads to T cell activation similar to the engagement of the T cell receptor but independent of its clone-typical specificity.

In one aspect is described herein a multispecific protein comprising a single domain serum albumin binding protein according to the present disclosure. In some embodiments, the multispecific protein further comprises a domain which specifically binds to CD3. In some embodiments, the multispecific protein further comprises a domain which specifically binds to human CD3. In some embodiments, the multispecific protein further comprises a domain which specifically binds to CD3γ. In some embodiments, the multispecific protein further comprises a domain which specifically binds to CD3δ. In some embodiments, the multispecific protein further comprises a domain which specifically binds to CD3ε.

In additional embodiments, the multispecific protein further comprises a domain which specifically binds to the T cell receptor (TCR). In some embodiments, the multispecific protein further comprises a domain which specifically binds the α chain of the TCR. In some embodiments, the multispecific protein further comprises a domain which specifically binds the β chain of the TCR.

In certain embodiments, the CD3 binding domain of the multispecific protein comprising a single domain serum albumin binding protein described herein exhibit not only potent CD3 binding affinities with human CD3, but show also excellent crossreactivity with the respective cynomolgus monkey CD3 proteins. In some instances, the CD3 binding domain of the multispecific proteins are cross-reactive with CD3 from cynomolgus monkey. In certain instances, human:cynomolgous $K_D$ (hKd: cKd) ratios for CD3 binding are between 20:1 and 1:2.

In some embodiments, the CD3 binding domain of the multispecific protein comprising a single domain serum albumin binding protein described herein can be any domain that binds to CD3 including but not limited to domains from a monoclonal antibody, a polyclonal antibody, a recombinant antibody, a human antibody, a humanized antibody, or antigen binding fragments of the CD3 binding antibodies, such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some instances, it is beneficial for the CD3 binding domain to be derived from the same species in which the multispecific protein comprising a single domain serum albumin binding protein described herein will ultimately be used in. For example, for use in humans, it may be beneficial for the CD3 binding domain of the multispecific protein comprising a single domain serum albumin binding protein described herein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3 binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3 binding domain described herein, e.g., a humanized or human anti-CD3 binding domain comprising one or more, e.g., all three, LC CDRs and one or more, e.g., all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lambda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

The affinity to bind to CD3 can be determined, for example, by the ability of the multispecific protein comprising a single domain serum albumin binding protein itself or its CD3 binding domain to bind to CD3 coated on an assay plate; displayed on a microbial cell surface; in solution; etc. The binding activity of multispecific protein comprising a single domain serum albumin binding protein itself or its CD3 binding domain according to the present disclosure to CD3 can be assayed by immobilizing the ligand (e.g., CD3) or said multispecific protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

Target Antigen Binding Domain

In addition to the described serum albumin binding and CD3 domains, the multispecific binding protein comprising a single domain serum albumin binding proteins described herein, in certain embodiments, also comprise a domain that binds to a target antigen. A target antigen is involved in and/or associated with a disease, disorder or condition. In particular, a target antigen associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In some embodiments, the target antigen is a tumor antigen expressed on a tumor cell. Alternatively in some embodiments, the target antigen is associated with a pathogen such as a virus or bacterium.

In some embodiments, the target antigen is a cell surface molecule such as a protein, lipid or polysaccharide. In some embodiments, the target antigen is a on a tumor cell, virally infected cell, bacterially infected cell, damaged red blood cell, arterial plaque cell, or fibrotic tissue cell.

The design of the multispecific binding proteins comprising a single domain serum albumin binding protein according to the present disclosure allows the binding domain to a target antigen to be flexible in that the binding domain to a target antigen can be any type of binding domain, including but not limited to, domains from a monoclonal antibody, a polyclonal antibody, a recombinant antibody, a human antibody, a humanized antibody. In some embodiments, the binding domain to a target antigen is a single chain variable fragments (scFv), single-domain antibody such as a heavy chain variable domain (VH), a light chain variable domain (VL) and a variable domain (VHH) of camelid derived sdAb. In other embodiments, the binding domain to a target antigen is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to a target antigen is a ligand or peptide that binds to or associates with a target antigen. In yet further embodiments, the binding domain to a target antigen is a knottin. In yet further embodiments, the binding domain to a target antigen is a small molecular entity.

Single Domain Serum Albumin Binding Protein Modifications

The single domain serum albumin binding proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence to block an immunogenic domain and/or for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in single domain serum albumin binding proteins described herein, including the peptide backbone, the amino acid side-chains, and the amino or carboxyl termini. Certain common peptide modifications that are useful for modification of single domain serum albumin binding proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation.

Polynucleotides Encoding Single Domain Serum Albumin Binding Proteins

Also provided, in some embodiments, are polynucleotide molecules encoding a single domain serum albumin binding protein described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells.

Also provided, in some embodiments, are polynucleotide molecules encoding a multispecific binding protein comprising a single domain serum albumin binding protein according to the present disclosure. In some embodiments, the polynucleotide encoding said multispecific binding protein also includes coding sequence for a CD3 binding domain. In some embodiments, the polynucleotide encoding said multispecific binding protein also includes coding sequence for a target antigen binding domain. In some embodiments, the polynucleotide encoding said multispecific binding protein also includes coding sequences for a CD3 binding domain and a target antigen binding domain. In some embodiments, the polynucleotide molecules are provided as a DNA construct. In other embodiments, the polynucleotide molecules are provided as a messenger RNA transcript. In the embodiments where the target antigen binding domain is a small molecule, the polynucleotides contain genes encoding the serum albumin binding domain and the CD3 binding domain. In the embodiments where the half-life extension domain is a small molecule, the polynucleotides contain genes encoding the domains that bind to CD3 and the target antigen. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described single domain serum albumin binding protein. Examples of expression vectors for expression in *E. coli* are pSKK (Le Gall et al., J Immunol Methods. (2004) 285(1): 111-27), pcDNA5 (Invitrogen) for expression in mammalian cells, PICHIAPINK™ Yeast Expression Systems (Invitrogen), BACUVANCE™ Baculovirus Expression System (GenScript).

Thus, the single domain serum albumin binding proteins as described herein, in some embodiments, are produced by introducing a vector encoding the protein as described above into a host cell and culturing said host cell under conditions whereby the protein domains are expressed, may be isolated and, optionally, further purified.

Production of Single Domain Serum Albumin Binding Proteins

Disclosed herein, in some embodiments, is a process for the production of a single domain serum albumin binding protein. In some embodiments, the process comprises culturing a host transformed or transfected with a vector comprising a nucleic acid sequence encoding a single domain serum albumin binding protein under conditions allowing the expression of the serum albumin binding protein and recovering and purifying the produced protein from the culture.

In an additional embodiment is provided a process directed to improving one or more properties, e.g. affinity, stability, heat tolerance, cross-reactivity, etc., of the single domain serum albumin binding proteins and/or the multispecific binding proteins comprising a single domain serum albumin binding protein described herein, compared to a reference binding compound. In some embodiments, a plurality of single-substitution libraries is provided each corresponding to a different domain, or amino acid segment of the single domain serum albumin binding protein or reference binding compound such that each member of the single-substitution library encodes only a single amino acid change in its corresponding domain, or amino acid segment. (This allows all of the potential substitutions in a large protein or protein binding site to be probed with a few small libraries.) In some embodiments, the plurality of domains forms or covers a contiguous sequence of amino acids of the single domain serum albumin binding protein or a reference binding compound. Nucleotide sequences of different single-substitution libraries overlap with the nucleotide sequences of at least one other single-substitution library. In some embodiments, a plurality of single-substitution libraries are designed so that every member overlaps every member of each single-substitution library encoding an adjacent domain.

Binding compounds expressed from such single-substitution libraries are separately selected to obtain a subset of variants in each library which has properties at least as good as those of the reference binding compound and whose resultant library is reduced in size. (That is, the number of nucleic acids encoding the selected set of binding compounds is smaller than the number of nucleic acids encoding members of the original single-substitution library) Such properties include, but are not limited to, affinity to a target compound, stability with respect to various conditions such as heat, high or low pH, enzymatic degradation, cross-reactivity to other proteins and the like. The selected compounds from each single-substitution library are referred to herein interchangeably as "pre-candidate compounds," or "pre-candidate proteins." Nucleic acid sequences encoding the pre-candidate compounds from the separate single-substitution libraries are then shuffled in a PCR to generate a shuffled library, using PCR-based gene shuffling techniques.

An exemplary work flow of the screening process is described herein. Libraries of pre-candidate compounds are generated from single substitution libraries and selected for binding to the target protein(s), after which the pre-candidate libraries are shuffled to produce a library of nucleic acids encoding candidate compounds which, in turn, are cloned into a convenient expression vector, such as a phagemid expression system. Phage expressing candidate compounds then undergo one or more rounds of selection for improvements in desired properties, such as binding affinity to a target molecule. Target molecules may be adsorbed or otherwise attached to a surface of a well or other reaction container, or target molecules may be derivatized with a binding moiety, such as biotin, which after incubation with candidate binding compounds may be captured with a complementary moiety, such as streptavidin, bound to beads, such as magnetic beads, for washing. In exemplary selection regimens, the candidate binding compounds undergo a prolonged wash step so that only candidate compounds with very low dissociation rates from a target molecule are selected. Exemplary wash times for such embodiments are at least 8 hours; or in other embodiments, at least 24 hours; or in other embodiments, at least 48 hours; or in other embodiments, at least 72 hours. Isolated clones after selection are amplified and subjected to an additional cycle of selection or analyzed, for example by sequencing and by making comparative measurements of binding affinity, for example, by ELISA, surface plasmon resonance binding, bio-layer interferometry (e.g. Octet system, ForteBio, Menlo Park, Calif.) or the like. In some embodiments, the process is implemented to identify one or more a single domain serum albumin binding proteins and/or a multispecific binding protein comprising a single domain serum albumin binding protein with improved thermal stability, improved cross reactivity to a selected set of binding targets compared to that of a reference serum albumin binding protein, such as a protein having the amino acid sequence of SEQ ID NO. 10. Single substitution libraries are prepared by varying codons in the VH region of the reference serum albumin binding protein, including both codons in framework regions and in CDRs; in another embodiment, the locations where codons are varied comprise the CDRs of the heavy chain of the reference serum albumin binding protein, or a subset of such CDRs, such as solely CDR1, solely CDR2, solely CDR3, or pairs thereof. In another embodiment, locations where codons are varied occur solely in framework regions. In some embodiments, a library comprises single codon changes solely from a reference serum albumin binding protein solely in framework regions of VH numbering in the range of from 10 to 250. In another embodiment, the locations where codons are varied comprise the CDR3s of the heavy chain of the reference serum albumin binding protein, or a subset of such CDR3s. In another embodiment, the number of locations where codons of VH encoding regions are varied are in the range of from 10 to 250, such that up to 100 locations are in framework region. After preparation of the single substitution library, as outlined above, the following steps are carried out: (a) expressing separately each member of each single substitution library as a pre-candidate protein; (b) selecting members of each single substitution library which encode pre-candidate proteins which bind to a binding partner that may or may not differ from the original binding target [e.g. a desired cross-reaction target(s)]; (c) shuffling members of the selected libraries in a PCR to produce a combinatorial shuffled library; (d) expressing members of the shuffled library as candidate serum albumin binding proteins; and (e) selecting members of the shuffled library one or more times for candidate serum albumin binding proteins which bind the original binding partner and potentially (f) further selecting the candidate proteins for binding to the desired cross-reactive target(s) thereby providing a nucleic acid encoded serum albumin binding protein with increased cross reactivity for the one or more substances with respect to the reference serum albumin binding protein without loss of affinity for the original ligand. In additional embodiments, the method may be implemented for obtaining a serum albumin binding protein with decreased reactivity to a selected cross-reactive substance(s) or compound(s) or epitope(s) by substituting step (f) with the following step: depleting candidate binding compounds one or more times from the subset of candidate serum albumin binding protein which bind to the undesired cross-reactive compound.

Recent studies have reported that during manufacturing, storage and in vivo use, therapeutic antibodies are at risk for degradation via a number of pathways. Amongst the most frequently occurring chemical degradation reactions in proteins are deamidation of asparagine (N) and isomerization of aspartic acid (D) residues. In particular, it has been hypothesized that if N and D residues are involved in antigen recognition, their chemical alteration can lead to severe loss of potency. Asparagine and aspartic acid residues are known to share a degradation pathway that proceeds via the formation of a cyclic succinimide intermediate. The formation of succinimide intermediates and their hydrolysis products (aspartate and isoaspartate), at the aspartic acid sites of an antibody represents a stability problem. When isomerization occurs, the chemical structure of the antibody alters, which could lead to poor stability, manifested for example by aggregation, shorter shelf-life. Accordingly, in some embodiments of the present disclosure are provided single domain serum albumin binding proteins wherein one or more aspartic acid residue is mutated, thereby reducing the isomerization potential of the single domain serum albumin binding protein. In some embodiments, the aspartic acid residue is in CDR2 of the single domain serum albumin binding protein and the aspartic acid residue is mutated to glutamic acid. In certain embodiments, the aspartic acid residue in position 62 of the protein defined by SEQ ID NO. 10 is mutated to glutamic acid (D62E). In some embodiments, the serum albumin binding affinity of the single domain serum albumin proteins containing the D62Emutation is not affected by the mutation. In some embodiments, single domain serum albumin binding proteins with and without the D62E mutation have comparable binding affinity towards serum albumin.

Pharmaceutical Compositions

Also provided, in some embodiments, are pharmaceutical compositions comprising a single domain serum albumin binding protein described herein, a vector comprising the polynucleotide encoding the polypeptide of the single domain serum albumin binding proteins or a host cell transformed by this vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

In some embodiments of the pharmaceutical compositions, the single domain serum albumin binding protein described herein is encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the single domain serum albumin binding protein is attached to liposomes. In some instances, the single domain serum albumin binding protein is conjugated to the surface of liposomes. In some instances, the single domain serum albumin binding protein is encapsulated within the shell of a liposome. In some instances, the liposome is a cationic liposome.

The single domain serum albumin binding proteins described herein are contemplated for use as a medicament. Administration is effected by different ways, e.g. by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

Methods of Treatment

Also provided herein, in some embodiments, are methods and uses for stimulating the immune system of an individual in need thereof comprising administration of a single domain serum albumin binding protein or a multispecific binding protein comprising the a single domain serum albumin binding protein described herein. In some instances, the administration of a single domain serum albumin binding protein described herein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue.

Also provided herein are methods and uses for a treatment of a disease, disorder or condition associated with a target antigen comprising administering to an individual in need thereof a single domain serum albumin binding protein or a multispecific binding protein comprising the a single domain serum albumin binding protein described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. In one instance, the cancer is a hematological cancer. In another instance, the cancer is a solid tumor cancer.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

In some embodiments of the methods described herein, the single domain serum albumin binding proteins or a multispecific binding protein comprising the a single domain serum albumin binding protein described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, the single domain serum albumin binding proteins or a multispecific binding protein comprising the a single domain serum albumin binding protein described herein are administered in combination with anti-diarrheal agents, anti-emetic agents, analgesics, opioids and/or non-steroidal anti-inflammatory agents. In some embodiments, the single domain serum albumin binding proteins or a multispecific binding protein comprising a single domain serum albumin binding protein as described herein are administered before, during, or after surgery.

EXAMPLES

Figure 2:
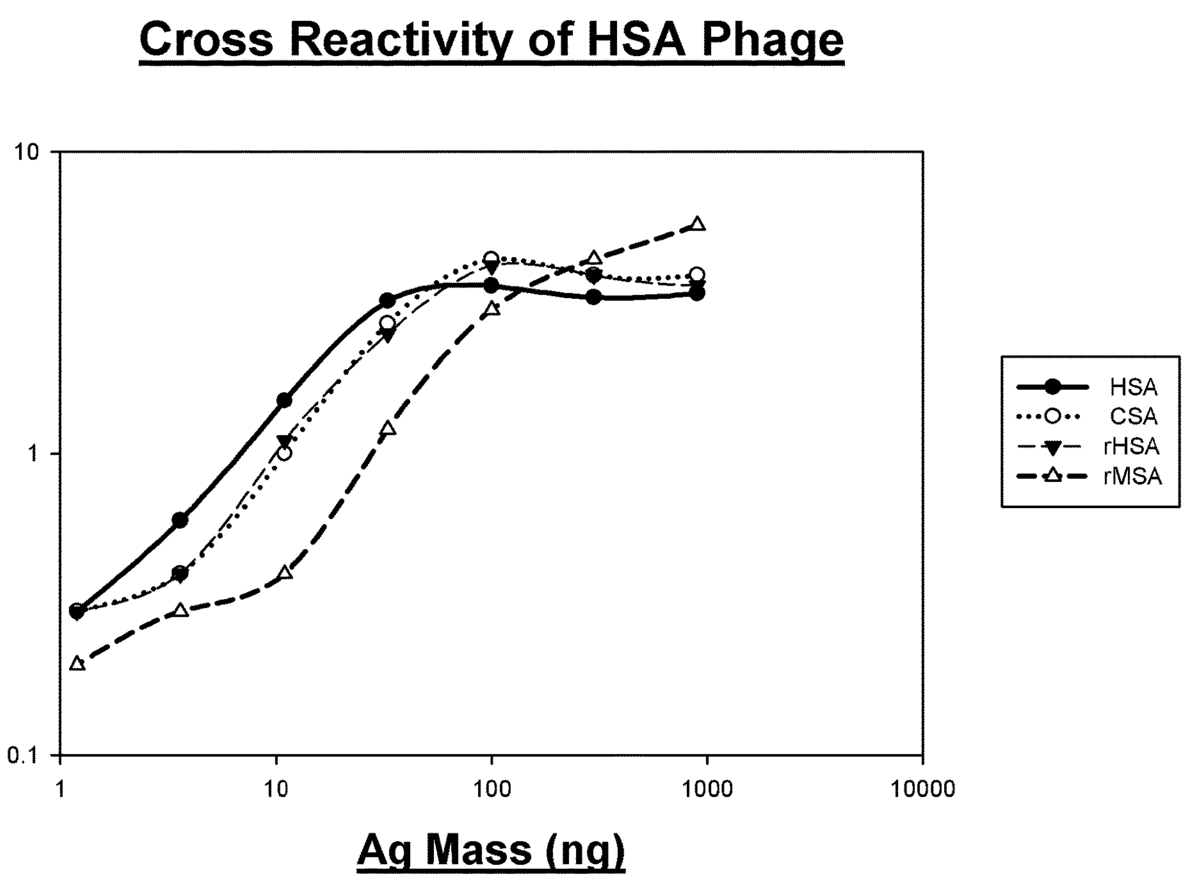
FIG. 2 illustrates the cross reactivity of anti-HSA phage to human, cynomolgus monkey, and mouse serum albumin as determined by ELISA titration.

Example 1: Generation of Anti-HSA Single Domain Antibody Variants with Equivalent Binding Properties to a Parental Anti-HSA Single Domain Antibody Characterization of Parental Anti-HSA Phage Specific binding of the parental anti-HSA phage to an HSA antigen was determined, using CD3 as a negative control (FIG. 1) and cross reactivity of the anti-HSA phage to human, cynomolgus monkey, and mouse serum albumin was determined (FIG. 2).

Single Substitution HSA sdAb Phage Libraries

A single substitution library was provided for each of the three CDR domains. Single substitution libraries were bound to HSA and then washed in buffer containing various levels of HSA. Phages bound at 0 and 24 hours were rescued and counted. Phages selected using a 24 hour wash with 2.5 mg/ml HSA in the buffer were used to create two independent combinatorial phage libraries.

Combinatorial Anti-HSA Libraries

MSA was used as the selection target in the first Round. Wells were washed for 24 hours after combinatorial phage binding from two independent libraries. HSA was used as the selection target in the second round. Wells were washed in 1 mg/ml HSA for 24 hours after binding of both libraries. Inserts PCRed from the second round of selection were subcloned into the ME10 His6 expression vector (6×His sequence disclosed as SEQ ID NO: 38). 96 clones were picked, DNA was purified, sequenced, and transfected into Expi293 cells.

Binding Affinity Measurement

Supernatants were used to estimate Kd to HSA and CSA using the Octet platform. Nine clones were selected for further characterization (FIG. 3), based on binding affinities compared to the parental sdAb as well as robust production, aggregation and stability profiles.

Example 2: Pharmacokinetics of a Trispecific Antibody Comprising the Anti-HSA Single Domain Antibody The anti-HSA single domain antibody of Example 1 is used to prepare a trispecific antibody which is evaluated for half-time elimination in animal studies.

The trispecific antibody is administered to cynomolgus monkeys as a 0.5 mg/kg bolus injection intramuscularly. Another cynomolgus monkey group receives a comparable protein in size with binding domains to CD3 and CD20, but lacking HSA binding. A third and fourth group receive an antibody with CD3 and HSA binding domains and a protein with CD20 and HSA binding domains respectively, and both comparable in size to the trispecific antibody. Each test group consists of 5 monkeys. Serum samples are taken at indicated time points, serially diluted, and the concentration of the proteins is determined using a binding ELISA to CD3 and/or CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and $\alpha$ and $\beta$ are the apparent first-order rate constants for the distribution and elimination phases, respectively. The $\alpha$-phase is the initial phase of the clearance and reflects distribution of the protein into all extracellular fluid of the animal, whereas the second or $\beta$-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and $\alpha$ and $\beta$ (for $\alpha>\beta$) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the trispecific antibody comprising the anti-HSA single domain antibody of Example 1 has improved pharmacokinetic parameters such as an increase in elimination half-time as compared to proteins lacking an HSA binding domain.

Example 3: Thermal Stability of Anti-HSA Single Domain Antibody Variants

The temperature of hydrophobic exposure ($T_h$) of a protein corresponds to the derivative of the inflection point of peak dye fluorescence and is known to correlate with melting temperature ($T_m$), which is a measure of protein stability. The goal of this study was to assess the $T_h$ for several anti-HAS single domain antibody variants.

Protein Production

Sequences of anti-huALB single domain antibodies were cloned into pcDNA3.4 (Invitrogen) preceded by a leader sequence and followed by a 6× Histidine tag (SEQ ID NO: 38). Expi293F cells (Life Technologies A14527) were maintained in suspension in Optimum Growth Flasks (Thomson) between 0.2 to 8×1e6 cells/ml in Expi 293 media. Purified plasmid DNA was transfected into Expi293F cells in accordance with Expi293 Expression System Kit (Life Technologies, A14635) protocols, and maintained for 4-6 days post transfection. Conditioned media was partially purified by affinity and desalting chromatography. Anti-huCD3e scFv proteins were concentrated with Amicon Ultra centrifugal filtration units (EMD Millipore), applied to Superdex 200 size exclusion media (GE Healthcare) and resolved in a neutral buffer containing excipients. Fraction pooling and final purity were assessed by SDS-PAGE and analytical size exclusion chromatography (SEC). The absorbance of purified protein solutions were determined at 280 nm using a SpectraMax M2 (Molecular Devices) and UV-transparent 96-well plates (Corning 3635) and their concentrations were calculated from molar extinction coefficients.

Differential Scanning Fluorimetry

Purified anti-HSA single domain antibody proteins were diluted from 0.2 to 0.25 mg/ml together with 5× SYPRO orange dye (Life Technologies S6651) in 0.15% DMSO final concentration in a neutral buffer containing excipients into MicroAmp EnduraPlate optical microplates and adhesive film (Applied Biosystems 4483485 and 4311971). A plate containing diluted protein and dye mixtures was loaded into an ABI 7500 Fast real-time PCR instrument (Applied Biosytems) and subjected to a multi-step thermal gradient from 25° C. to 95° C. The thermal gradient comprised of a two minute hold at each one degree Celsius with excitation at 500 nm and emission collected with a ROX filter. $T_h$ in degrees celsius is presented for purified anti-HSA single domain antibody proteins in FIG. 4.

Example 4: Relative Propensity of Dimerization of Anti-HSA Single Domain Antibody Variants when Exposed to Low pH Anti-HSA single domain antibody proteins were expressed in Expi293-F cells as above. Conditioned medium for each variant was applied to protein A agarose (GE Healthcare, 17519901) packed in a column, washed extensively with TRIS buffered saline, eluted with 0.05% (vol/vol) acetic acid at pH 3, held at room temperature for up to ten minutes prior to partial neutralization to pH 5, and subsequently desalted into a neutral buffer containing excipients using Sephadex G25 columns (GE Healthcare 17058401).

Concentrations of purified anti-HSA single domain antibody variants were determined by absorbance at 280 nm as described in Example 3. Purified proteins were evaluated by SDS-PAGE and analytical SEC using a Yarra 2000 SEC column (Phenomenex 00H-4512-EO) resolved in phosphate buffer containing solvent on a 1200 LC with Chemstation software (Agilent). Peaks corresponding to dimer and monomer were manually integrated and values are presented in FIG. 5.

| SEQ ID NO: | Description | AA Sequence |
|---|---|---|
| 1 | CDR1 with variant positions | $GFX_1X_2X_3X_4FGMS$ |
| 2 | CDR2 with variant positions | $SISGSGX_5X_6TLYAX_7SX_8K$ |

-continued

| SEQ ID NO: | Description | AA Sequence |
|---|---|---|
| 3 | CDR3 with variant positions | GGSL$X_9X_{10}$ |
| 4 | Anti-HSA sdAb clone 6C | EVQLVESGGGLVQPGNSLRLSCAASGFTFSRFGMSWVRQAPGKGL EWVSSISGSGSDTLYADSVKGRFTISRDNAKTTLYLQMNSLRPEDTA VYYCTIGGSLSRSSQGTLVTVSS |
| 5 | Anti-HSA sdAb clone 7A | EVQLVESGGGLVQPGNSLRLSCAASGFTFSKFGMSWVRQAPGKGL EWVSSISGSGADTLYADSLKGRFTISRDNAKTTLYLQMNSLRPEDT AVYYCTIGGSLSKSSQGTLVTVSS |
| 6 | Anti-HSA sdAb clone 7G | EVQLVESGGGLVQPGNSLRLSCAASGFTYSSFGMSWVRQAPGKGL EWVSSISGSGSDTLYADSVKGRFTISRDNAKTTLYLQMNSLRPEDTA VYYCTIGGSLSKSSQGTLVTVSS |
| 7 | Anti-HSA sdAb clone 8H | EVQLVESGGGLVQPGNSLRLSCAASGFTFSKFGMSWVRQAPGKGL EWVSSISGSGTDTLYADSVKGRFTISRDNAKTTLYLQMNSLRPEDT AVYYCTIGGSLSRSSQGTLVTVSS |
| 8 | Anti-HSA sdAb clone 9A | EVQLVESGGGLVQPGNSLRLSCAASGFTFSRFGMSWVRQAPGKGL EWVSSISGSGSDTLYADSVKGRFTISRDNAKTTLYLQMNSLRPEDTA VYYCTIGGSLSKSSQGTLVTVSS |
| 9 | Anti-HSA sdAb clone 10G | EVQLVESGGGLVQPGNSLRLSCAASGFTFSKFGMSWVRQAPGKGL EWVSSISGSGRDTLYADSVKGRFTISRDNAKTTLYLQMNSLRPEDT AVYYCTIGGSLSVSSQGTLVTVSS |
| 10 | wt anti-HSA | EVQLVESGGGLVQPGNSLRLSCAASGFTFSSFGMSWVRQAPGKGLE WVSSISGSGSDTLYADSVKGRFTISRDNAKTTLYLQMNSLRPEDTA VYYCTIGGSLSRSSQGTLVTVSS |
| 11 | wt anti-HSA CDR1 | GFTFSSFGMS |
| 12 | wt anti-HSA CDR2 | SISGSGSDTLYADSVK |
| 13 | wt anti-HSACDR3 | GGSLSR |
| 14 | CDR1 variant 1 | GFTFSRFGMS |
| 15 | CDR1 variant 2 | GFTFSKFGMS |
| 16 | CDR1 variant 3 | GFTYSSFGMS |
| 17 | CDR2 variant 1 | SISGSGADTLYADSLK |
| 18 | CDR2 variant 2 | SISGSGTDTLYADSVK |
| 19 | CDR2 variant 3 | SISGSGRDTLYADSVK |
| 20 | CDR2 variant 4 | SISGSGSDTLYAESVK |
| 21 | CDR2 variant 5 | SISGSGTDTLYAESVK |
| 22 | CDR2 variant 6 | SISGSGRDTLYAESVK |
| 23 | CDR3 variant 1 | GGSLSK |
| 24 | CDR3 variant 2 | GGSLSV |
| 25 | Anti-HSA sdAb clone 6CE | EVQLVESGGGLVQPGNSLRLSCAASGFTFSRFGMSWVRQAPGKGL EWVSSISGSGSDTLYAESVKGRFTISRDNAKTTLYLQMNSLRPEDTA VYYCTIGGSLSRSSQGTLVTVSS |
| 26 | Anti-HSA sdAb clone 8HE | EVQLVESGGGLVQPGNSLRLSCAASGFTFSKFGMSWVRQAPGKGL EWVSSISGSGTDTLYAESVKGRFTISRDNAKTTLYLQMNSLRPEDTA VYYCTIGGSLSRSSQGTLVTVSS |
| 27 | Anti-HSA sdAb clone 10GE | EVQLVESGGGLVQPGNSLRLSCAASGFTFSKFGMSWVRQAPGKGL EWVSSISGSGRDTLYAESVKGRFTISRDNAKTTLYLQMNSLRPEDTA VYYCTIGGSLSVSSQGTLVTVSS |
| 28 | Exemplary linker sequence | (GS)n |
| 29 | Exemplary linker sequence | (GGS)n |
| 30 | Exemplary linker sequence | (GGGS)n |

-continued

| SEQ ID NO: | Description | AA Sequence |
|---|---|---|
| 31 | Exemplary linker sequence | (GGSG)n |
| 32 | Exemplary linker sequence | (GGSGG)n |
| 33 | Exemplary linker sequence | (GGGGS)n |
| 34 | Exemplary linker sequence | (GGGGG)n |
| 35 | Exemplary linker sequence | (GGG)n |
| 36 | Exemplary linker sequence | (GGGGS)3 |
| 37 | Exemplary linker sequence | (GGGGS)4 |
| 38 | 6X Histidine | HHHHHH |

What is claimed is:

1. A multispecific protein comprising a serum albumin binding domain, a target antigen binding domain, and a domain that binds to a protein within a T cell receptor complex (TCR), wherein the serum albumin binding domain comprises complementarity determining regions CDR1, CDR2, and CDR3, wherein (a) the amino acid sequence of CDR1 is as set forth in $GFX_1X_2X_3X_4FGMS$ (SEQ ID NO. 1), $X_1$ is threonine, arginine, lysine, serine, or proline, $X_2$ is phenylalanine or tyrosine, $X_3$ is serine, arginine or lysine, $X_4$ is serine, lysine, arginine, or alanine;

(b) the amino acid sequence of CDR2 is as set forth in $SISGSGX_5X_6TLYAX_7SX_8K$ (SEQ ID NO. 2), $X_5$ is serine, arginine, threonine, or alanine, $X_6$ is aspartic acid, histidine, valine, or threonine, $X_7$ is aspartic acid, histidine, arginine, or serine, $X_8$ is valine or leucine; and (c) the amino acid sequence of CDR3 is as set forth in $GGSLX_9X_{10}$ (SEQ ID NO. 3), $X_9$ is serine, arginine, threonine, or lysine, and $X_{10}$ is arginine, lysine, valine, proline, or asparagine, wherein $X_1$, $X_2$, $X_3$, $X_4$, $X_5$, $X_6$, $X_7$, $X_8$, $X_9$, and $X_{10}$ are not simultaneously threonine, phenylalanine, serine, serine, serine, aspartic acid, aspartic acid, valine, serine, and arginine, respectively.

2. The multispecific protein of claim 1, wherein the serum albumin binding domain is at least eighty percent identical to the amino acid sequence set forth in SEQ ID NO. 10.

3. The multispecific protein of claim 1, wherein the CDR1 has an amino acid sequence as set forth in SEQ ID NO. 14, SEQ ID NO. 15 or SEQ ID NO. 16.

4. The multispecific protein of claim 1, wherein the CDR2 has an amino acid sequence as set forth in SEQ ID NO. 17, SEQ ID NO. 18, SEQ ID NO. 19, SEQ ID NO. 20, SEQ ID NO. 21, or SEQ ID NO. 22.

5. The multispecific protein of claim 1, wherein the CDR3 has an amino acid sequence as set forth in SEQ ID NO. 23 or SEQ ID NO. 24.

6. The multispecific protein of claim 1, wherein the CDR1 has an amino acid sequence as set forth in SEQ ID NO. 14.

7. The multispecific protein of claim 1, wherein the CDR1 has an amino acid sequence as set forth in SEQ ID NO. 15, the CDR2 has an amino acid sequence as set forth in SEQ ID NO. 17, and the CDR3 has an amino acid sequence as set forth in SEQ ID NO.23.

8. The multispecific protein of claim 1, wherein the CDR1 has an amino acid sequence as set forth in SEQ ID NO. 16, and the CDR3 has an amino acid sequence as set forth in SEQ ID NO. 23.

9. The multispecific protein of claim 1, wherein the CDR1 has an amino acid sequence as set forth in SEQ ID NO. 15 and the CDR2 has an amino acid sequence as set forth in SEQ ID NO. 18.

10. The multispecific protein of claim 1, wherein the CDR1 has an amino acid sequence as set forth in SEQ ID NO. 14 and the CDR3 has an amino acid sequence as set forth in SEQ ID NO. 23.

11. The multispecific protein of claim 1, wherein the CDR1 has an amino acid sequence as set forth in SEQ ID NO. 15, [r2] the CDR2 comprises SEQ ID NO. 19 and [r3] the CDR3 comprises SEQ ID NO. 24.

12. The multispecific protein of claim 1, wherein the CDR1 has an amino acid sequence as set forth in SEQ ID NO. 14 and the CDR2 has an amino acid sequence as set forth in SEQ ID NO. 20.

13. The multispecific protein of claim 1, wherein the CDR1 has an amino acid sequence as set forth in SEQ ID NO. 15, and the CDR2 has an amino acid sequence as set forth in SEQ ID NO. 21.

14. The multispecific protein of claim 1, wherein the CDR1 has an amino acid sequence as set forth in SEQ ID NO. 15, the CDR2 has an amino acid sequence as set forth in SEQ ID NO. 22 and the CDR3 has an amino acid sequence as set forth in SEQ ID NO. 24.

15. The multispecific protein of claim 1, wherein the target antigen binding domain binds to a target antigen expressed on a tumor cell.

16. The multispecific protein of claim 1, wherein the protein within the T cell receptor complex (TCR) is CD3.

17. The multispecific protein of claim 1, wherein the serum albumin binding domain has an amino acid sequence selected from SEQ ID NO. 4, SEQ ID NO. 5, SEQ ID NO. 6, SEQ ID NO. 7, SEQ ID NO. 8, SEQ ID NO. 9, SEQ ID NO. 25, SEQ ID NO. 26, and SEQ ID NO. 27.

18. A multispecific protein comprising a serum albumin binding domain, a target antigen binding domain, and a domain that binds to a protein within a T cell receptor complex (TCR), wherein the serum albumin binding domain comprises complementarity determining regions CDR1, CDR2, and CDR3 within the sequence set forth as SEQ ID NO. 10 (wt anti-HSA), wherein one or more amino acid residues selected from amino acid positions 28, 29, 30, or 31 of CDR1; positions 56, 57, 62, or 64 of CDR2; and positions 103, and 104 of CDR3 are substituted, wherein amino acid position 28 is substituted with arginine, lysine, serine, or proline, amino acid position 29 is substituted with tyrosine, amino acid position 30 is substituted with arginine or lysine, amino acid position 31 is substituted with lysine, arginine, or alanine, amino acid position 56 is substituted with arginine, threonine, or alanine, amino acid position 57 is substituted with histidine, valine, or threonine, amino acid position 62 is substituted with histidine, arginine, glutamic acid, or serine, amino acid position 64 is substituted with leucine, amino acid position 103 is substituted with arginine, threonine, or lysine, amino acid position 104 is substituted with lysine, valine, proline, or asparagine.

19. A multispecific protein comprising a serum albumin binding domain, a target antigen binding domain, and a domain that binds to a protein within a T cell receptor complex (TCR), wherein the serum albumin protein comprises at least one mutation in CDR1, CDR2 or CDR3, wherein CDR1 has the sequence as set forth is SEQ ID NO:11, CDR2 has the sequence as set forth in SEQ ID NO:12, CDR3 has the sequence as set forth in SEQ ID NO. 13, and wherein the at least one mutation is not in amino acid positions 1, 2, 7, 8, 9, or 10 of SEQ ID NO: 11, positions 1, 3, 6, 10, or 11 of SEQ ID NO: 12, or positions 1 or 2 of SEQ ID NO: 13.

20. The multispecific protein of claim 19, comprising at least one mutation in amino acid positions selected from positions 3, 4, 5, and 6 of CDR1 (SEQ ID NO: 11), amino acid positions 7, 8, 13, and 15 of CDR2 (SEQ ID NO: 12), and amino acid positions 5 and 6 of CDR3 (SEQ ID NO: 13).

* * * * *

UNITED STATES PATENT AND TRADEMARK OFFICE

CERTIFICATE OF CORRECTION

PATENT NO. : 11,453,716 B2
APPLICATION NO. : 16/161986
DATED : September 27, 2022
INVENTOR(S) : Robert B. Dubridge et al.

It is certified that error appears in the above-identified patent and that said Letters Patent is hereby corrected as shown below:

In the Claims

In Column 51, Line 38, Claim 1, (a), please add -- wherein -- before "$X_1$"

In Column 51, Line 40, Claim 1, (a), please add -- and -- before "$X_4$"

In Column 51, Line 43, Claim 1, (b), please add -- wherein -- before "$X_5$"

In Column 51, Line 46, Claim 1, (b), please add -- and -- before "$X_8$"

In Column 51, Line 49, Claim 1, (c), please add -- wherein -- before "$X_9$"

In Column 51, Line 51, Claim 1, (c), please delete the "," after "asparagine" and add -- ; and --

In Column 52, Line 50, Claim 11, please delete "[r2]" and "[r3]"

In Column 53, Line 5, Claim 17, please add -- the group consisting of -- before "SEQ ID NO. 4,"

In Column 53, Line 15, Claim 18, please add -- among -- before "amino"

In Column 53, Line 15, Claim 18, please replace "positions" with -- position --

In Column 53, Line 16, Claim 18, please delete the word "positions" in two instances, and replace with -- amino acid position -- for both instances In Column 54, Line 5, Claim 18, add -- or -- after "lysine,"

In Column 54, Line 12, Claim 19, replace "CDR1, CDR2 or CDR3," with -- a CDR1, a CDR2 or a CDR3, --

Signed and Sealed this
Tenth Day of October, 2023

Katherine Kelly Vidal

Katherine Kelly Vidal
*Director of the United States Patent and Trademark Office*

In Column 54, Line 13, Claim 19, add -- the -- before “CDR1”

In Column 54, Line 14, Claim 19, add -- the -- before “CDR2”

In Column 54, Line 15, Claim 19, add -- and the -- before “CDR3”

In Column 54, Line 17, Claim 19, replace “positions 1, 2, 7, 8, 9 or 10 of SEQ ID NO:11, positions 1,” with -- position 1, 2, 7, 8, 9, or 10 of SEQ ID NO: 11, amino acid position 1, --

In Column 54, Line 18, Claim 19, please replace “positions” with -- amino acid position --

In Column 54, Line 22, Claim 20, please replace “positions 3, 4, 5, and 6 of CDR1” with -- among positions 3, 4, 5, and 6 of the CDR1 --

In Column 54, Line 23, Claim 20, please add -- the -- before “CDR2”

In Column 54, Line 24, Claim 20, please add -- the -- before “CDR3”

SEQUENCE LISTING

<160> NUMBER OF SEQ ID NOS: 38

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Thr, Arg, Lys, Ser or Pro
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (5)..(5)
<223> OTHER INFORMATION: Ser, Arg or Lys
<220> FEATURE:
<221> NAME/KEY: MOD_RES
<222> LOCATION: (6)..(6)
<223> OTHER INFORMATION: Ser, Lys, Arg or Ala

<400> SEQUENCE: 1

Gly Phe Xaa Xaa Xaa Xaa Phe Gly Met Ser
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ser, Arg, Thr or Ala
<220> FEATURE:
<221> NAME/KEY: MOD_RES
<222> LOCATION: (8)..(8)
<223> OTHER INFORMATION: Asp, His, Val or Thr
<220> FEATURE:
<221> NAME/KEY: MOD_RES
<222> LOCATION: (13)..(13)
<223> OTHER INFORMATION: Asp, His, Arg or Ser
<220> FEATURE:

```
<221> NAME/KEY: MOD_RES
<222> LOCATION: (15)..(15)
<223> OTHER INFORMATION: Val or Leu

<400> SEQUENCE: 2

Ser Ile Ser Gly Ser Gly Xaa Xaa Thr Leu Tyr Ala Xaa Ser Xaa Lys
1               5                   10                  15


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Arg, Thr or Lys
<220> FEATURE:
<221> NAME/KEY: MOD_RES
<222> LOCATION: (6)..(6)
<223> OTHER INFORMATION: Arg, Lys, Val, Pro or Asn

<400> SEQUENCE: 3

Gly Gly Ser Leu Xaa Xaa
1               5


<210> SEQ ID NO 4
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 5
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Gln Pro Gly Asn
1               5                   10                  15
```

```
Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ala Asp Thr Leu Tyr Ala Asp Ser Leu
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115


<210> SEQ ID NO 6
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Tyr Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115


<210> SEQ ID NO 7
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Asp Ser Val
    50                  55                  60
```

```
Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 8
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115


<210> SEQ ID NO 9
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110
```

```
Val Ser Ser
        115


<210> SEQ ID NO 10
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Thr Phe Ser Ser Phe Gly Met Ser
1               5                   10


<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ile Ser Gly Ser Gly Ser Asp Thr Leu Tyr Ala Asp Ser Val Lys
1               5                   10                  15


<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Ser Leu Ser Arg
```

1 5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gly Phe Thr Phe Ser Arg Phe Gly Met Ser
1 5 10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Gly Phe Thr Phe Ser Lys Phe Gly Met Ser
1 5 10

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 16

Gly Phe Thr Tyr Ser Ser Phe Gly Met Ser
1 5 10

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Ser Ile Ser Gly Ser Gly Ala Asp Thr Leu Tyr Ala Asp Ser Leu Lys
1 5 10 15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Ser Ile Ser Gly Ser Gly Thr Asp Thr Leu Tyr Ala Asp Ser Val Lys
1 5 10 15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Ser Ile Ser Gly Ser Gly Arg Asp Thr Leu Tyr Ala Asp Ser Val Lys
1 5 10 15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Ser Ile Ser Gly Ser Gly Ser Asp Thr Leu Tyr Ala Glu Ser Val Lys
1 5 10 15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Ser Ile Ser Gly Ser Gly Thr Asp Thr Leu Tyr Ala Glu Ser Val Lys
1 5 10 15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Ser Ile Ser Gly Ser Gly Arg Asp Thr Leu Tyr Ala Glu Ser Val Lys
1 5 10 15

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gly Gly Ser Leu Ser Lys
1 5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Gly Gly Ser Leu Ser Val
1 5

<210> SEQ ID NO 25

```
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 26
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Glu Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115


<210> SEQ ID NO 27
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27
```

-continued

Glu Val Gln Leu Val Glu Ser Gly Gly Gly Leu Val Gln Pro Gly Asn
1 5 10 15

Ser Leu Arg Leu Ser Cys Ala Ala Ser Gly Phe Thr Phe Ser Lys Phe
20 25 30

Gly Met Ser Trp Val Arg Gln Ala Pro Gly Lys Gly Leu Glu Trp Val
35 40 45

Ser Ser Ile Ser Gly Ser Gly Arg Asp Thr Leu Tyr Ala Glu Ser Val
50 55 60

Lys Gly Arg Phe Thr Ile Ser Arg Asp Asn Ala Lys Thr Thr Leu Tyr
65 70 75 80

Leu Gln Met Asn Ser Leu Arg Pro Glu Asp Thr Ala Val Tyr Tyr Cys
85 90 95

Thr Ile Gly Gly Ser Leu Ser Val Ser Ser Gln Gly Thr Leu Val Thr
100 105 110

Val Ser Ser
115

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence: Synthetic Peptide
<220> FEATURE:
<221> NAME/KEY: MISC_FEATURE
<222> LOCATION: (1)..(20)
<223> OTHER INFORMATION: This region may encompass 1-10 “Gly Ser” repeating units

<400> SEQUENCE: 28

Gly Ser Gly Ser Gly Ser Gly Ser Gly Ser Gly Ser Gly Ser Gly Ser
1 5 10 15

Gly Ser Gly Ser
20

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This region may encompass 1-10 “Gly Gly Ser” repeating units

<400> SEQUENCE: 29

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Gly Gly Ser
20 25 30

<210> SEQ ID NO 30
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(40)

-continued

```
<223> OTHER INFORMATION: This region may encompass 1-10 "Gly Gly Gly
      Ser" repeating units

<400> SEQUENCE: 30

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40


<210> SEQ ID NO 31
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This region may encompass 1-10 "Gly Gly Ser
      Gly" repeating units

<400> SEQUENCE: 31

Gly Gly Ser Gly Gly Gly Ser Gly Gly Gly Ser Gly Gly Gly Ser Gly
1               5                   10                  15

Gly Gly Ser Gly Gly Gly Ser Gly Gly Gly Ser Gly Gly Gly Ser Gly
            20                  25                  30

Gly Gly Ser Gly Gly Gly Ser Gly
        35                  40


<210> SEQ ID NO 32
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This region may encompass 1-10 "Gly Gly Ser Gly
      Gly" repeating units

<400> SEQUENCE: 32

Gly Gly Ser Gly Gly Gly Gly Ser Gly Gly Gly Gly Ser Gly Gly Gly
1               5                   10                  15

Gly Ser Gly Gly Gly Gly Ser Gly Gly Gly Gly Ser Gly Gly Gly Gly
            20                  25                  30

Ser Gly Gly Gly Gly Ser Gly Gly Gly Gly Ser Gly Gly Gly Gly Ser
        35                  40                  45

Gly Gly
    50


<210> SEQ ID NO 33
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This region may encompass 1-10 "Gly Gly Gly Gly
```

Ser” repeating units

<400> SEQUENCE: 33

Gly Gly Gly Gly Ser Gly Gly Gly Gly Ser Gly Gly Gly Gly Ser Gly
1 5 10 15

Gly Gly Gly Ser Gly Gly Gly Gly Ser Gly Gly Gly Gly Ser Gly Gly
20 25 30

Gly Gly Ser Gly Gly Gly Gly Ser Gly Gly Gly Gly Ser Gly Gly Gly
35 40 45

Gly Ser
50

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(50)
<223> OTHER INFORMATION: This region may encompass 1-10 “Gly Gly Gly Gly Gly” repeating units

<400> SEQUENCE: 34

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly Gly Gly
20 25 30

Gly Gly Gly Gly Gly Gly Gly Gly Gly Gly Gly Gly Gly Gly Gly Gly
35 40 45

Gly Gly
50

<210> SEQ ID NO 35
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<222> LOCATION: (1)..(30)
<223> OTHER INFORMATION: This region may encompass 1-10 “Gly Gly Gly” repeating units

<400> SEQUENCE: 35

Gly Gly Gly Gly Gly Gly Gly Gly Gly Gly Gly Gly Gly Gly Gly Gly
1 5 10 15

Gly Gly Gly Gly Gly Gly Gly Gly Gly Gly Gly Gly Gly Gly
20 25 30

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gly Gly Gly Gly Ser Gly Gly Gly Gly Ser Gly Gly Gly Gly Ser
1 5 10 15

-continued

```
<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Gly Gly Ser Gly Gly Gly Gly Ser Gly Gly Gly Gly Ser Gly
1               5                   10                  15

Gly Gly Gly Ser
            20


<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 38

His His His His His His
1               5
```